United States Patent [19]

Nakao et al.

[11] Patent Number: 5,049,153
[45] Date of Patent: Sep. 17, 1991

[54] ENDOSCOPIC STAPLING DEVICE AND METHOD

[76] Inventors: Naomi L. Nakao, 303 E. 57th St., New York, N.Y. 10022; Peter J. Wilk, 185 West End Ave., New York, N.Y. 10023

[21] Appl. No.: 543,704

[22] Filed: Jun. 26, 1990

Related U.S. Application Data

[63] Continuation-in-part of Ser. No. 456,960, Dec. 26, 1989, Pat. No. 5,015,249.

[51] Int. Cl.$^5$ .............................................. A61B 17/00
[52] U.S. Cl. ..................................... 606/151; 606/138; 606/143
[58] Field of Search ............... 606/138, 139, 142, 143, 606/151, 157, 174, 205; 128/4, 6, 751

[56] References Cited

U.S. PATENT DOCUMENTS

| | | | |
|---|---|---|---|
| 943,263 | 12/1909 | Moraneck | 606/205 |
| 1,510,416 | 9/1924 | Pietz et al. | 606/205 |
| 2,113,246 | 4/1938 | Wappler | 606/205 |
| 2,968,041 | 1/1961 | Skold . | |
| 3,378,010 | 4/1968 | Codling et al. | 606/157 |
| 3,518,993 | 7/1970 | Blake . | |
| 3,882,854 | 5/1975 | Hulka et al. . | |
| 3,958,576 | 5/1976 | Komiya . | |
| 4,038,987 | 8/1977 | Komiya | 606/142 |
| 4,367,746 | 1/1983 | Derechinsky . | |
| 4,394,861 | 7/1983 | Sandhaus . | |
| 4,446,865 | 5/1984 | Jewusiak | 606/142 |
| 4,485,817 | 12/1984 | Swiggett . | |
| 4,496,090 | 1/1985 | Creiver et al. . | |
| 4,681,107 | 7/1987 | Kees, Jr. . | |
| 4,706,668 | 11/1987 | Backer . | |
| 4,714,075 | 12/1987 | Krauter et al. | 128/4 |
| 4,735,194 | 4/1988 | Stiegmann | 128/6 |
| 4,759,364 | 7/1988 | Boebel . | |
| 4,796,627 | 1/1989 | Tucker . | |
| 4,821,721 | 4/1989 | Chin et al. . | |
| 4,841,888 | 6/1989 | Mills et al. . | |
| 4,880,015 | 11/1989 | Nierman | 128/751 |
| 4,887,612 | 12/1989 | Esser et al. | 606/174 |
| 4,945,920 | 8/1990 | Clossick | 606/205 |
| 4,971,067 | 11/1990 | Bolduc et al. | 128/751 |
| 4,983,176 | 1/1991 | Cushman et al. | 606/151 |

Primary Examiner—David J. Isabella
Assistant Examiner—Elizabeth M. Burke
Attorney, Agent, or Firm—R. Neil Sudol; Henry D. Coleman

[57] ABSTRACT

A surgical instrument comprises an elongate flexible forceps member having a diameter sufficiently small so that the forceps member is slidably insertable into a biopsy channel extending longitudinally through a flexible tubular endoscope member, the forceps member being provided at a distal end with a pair of forceps jaws each formed on an inwardly facing surface with a longitudinally extending groove. A staple having a spring bias construction tending to force the staple into an opened configuration is disposed in a closed prefiring configuration between the jaws and has a pair of legs each disposed in the closed prefiring configuration in a respective one of the grooves in the forceps jaws. The provided with locking elements for locking the staple in a closed postfiring configuration.

21 Claims, 15 Drawing Sheets

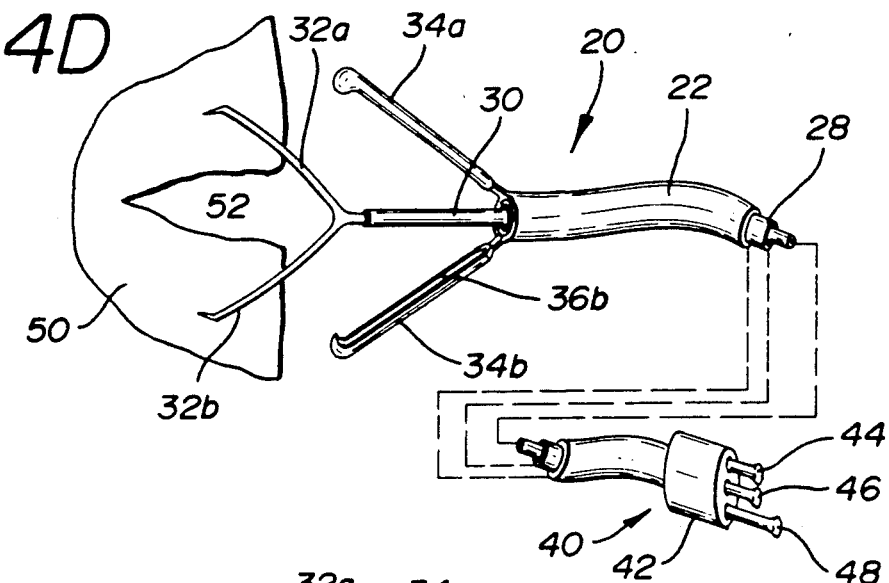
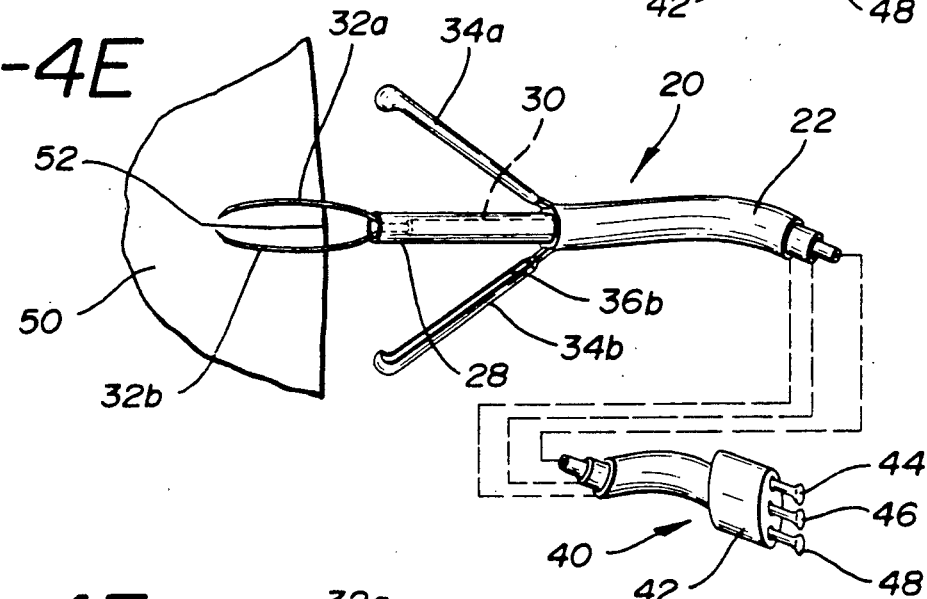
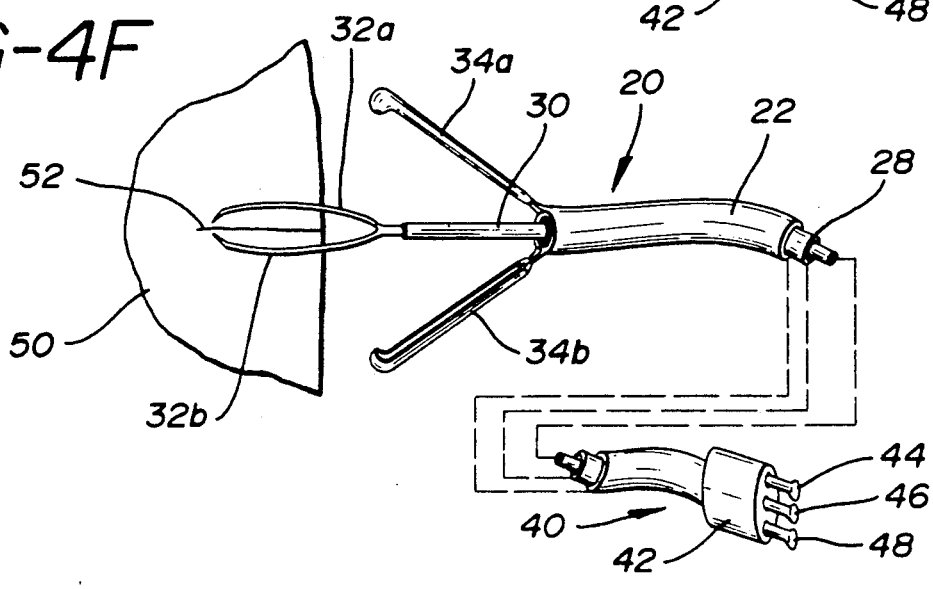

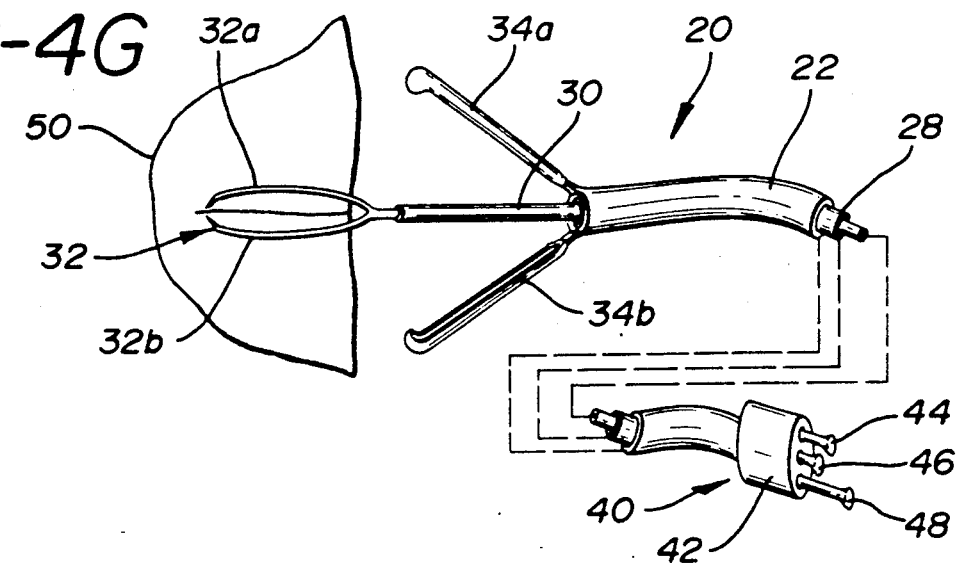
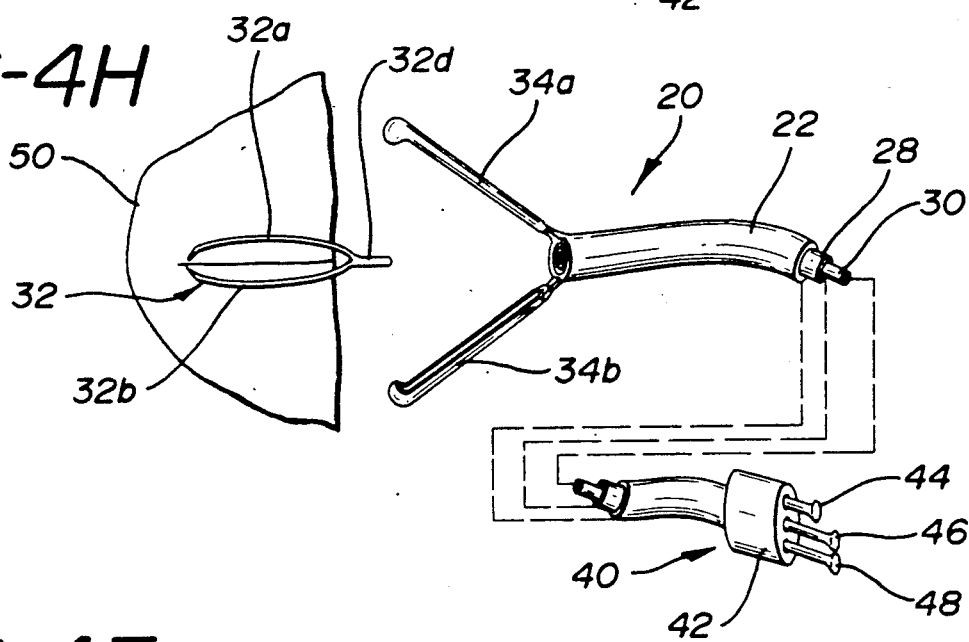
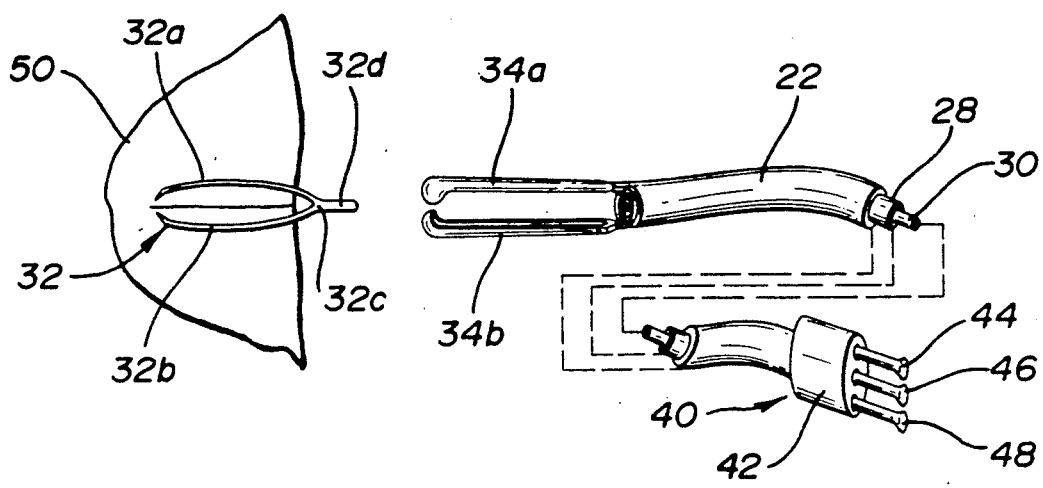

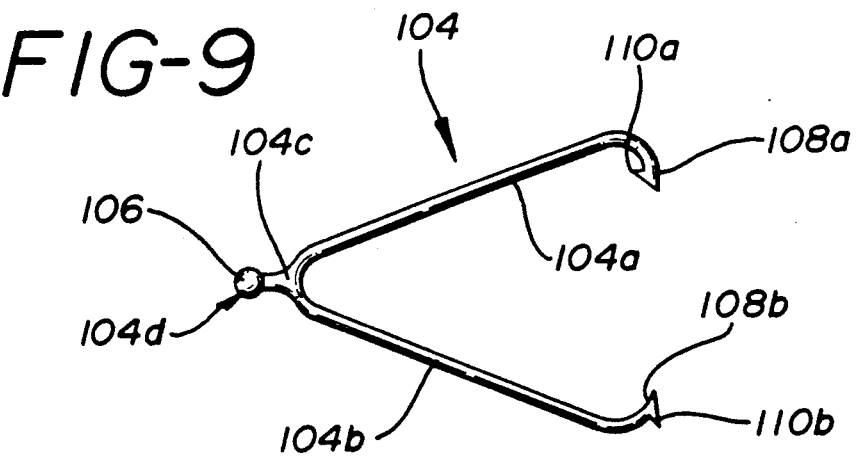
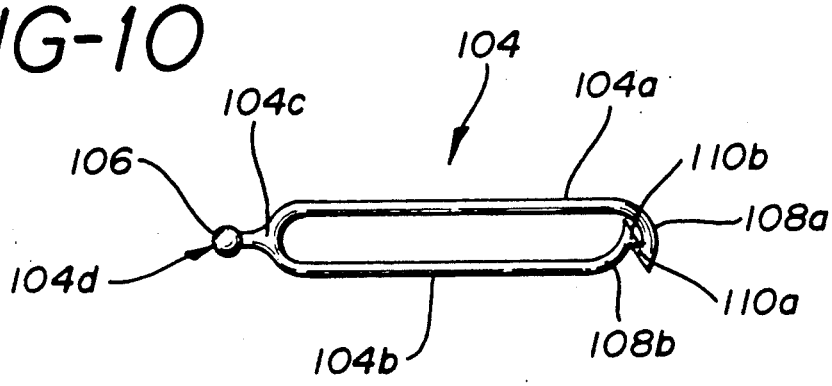
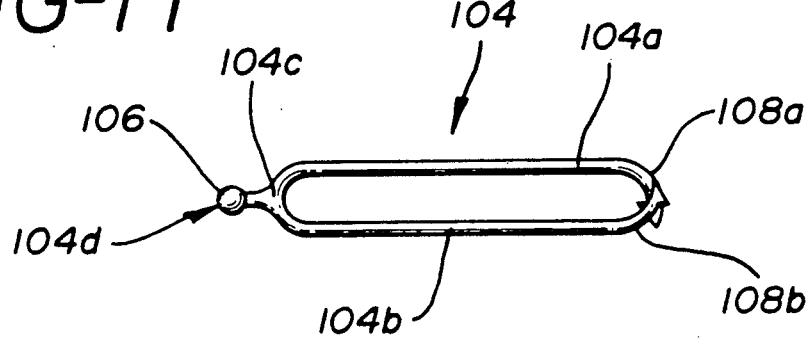
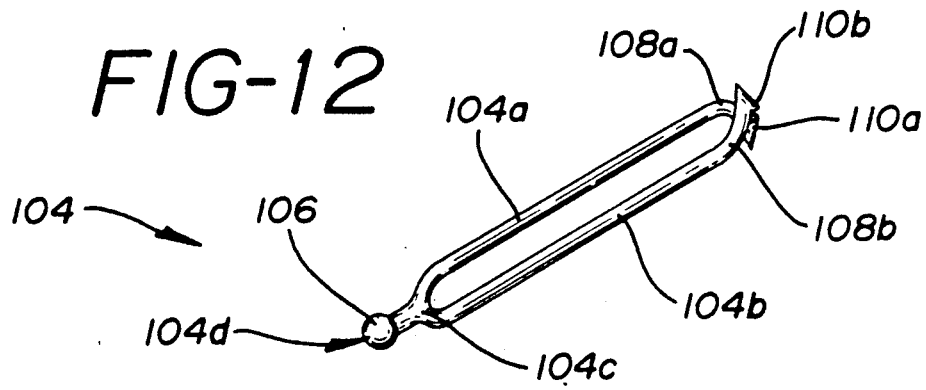

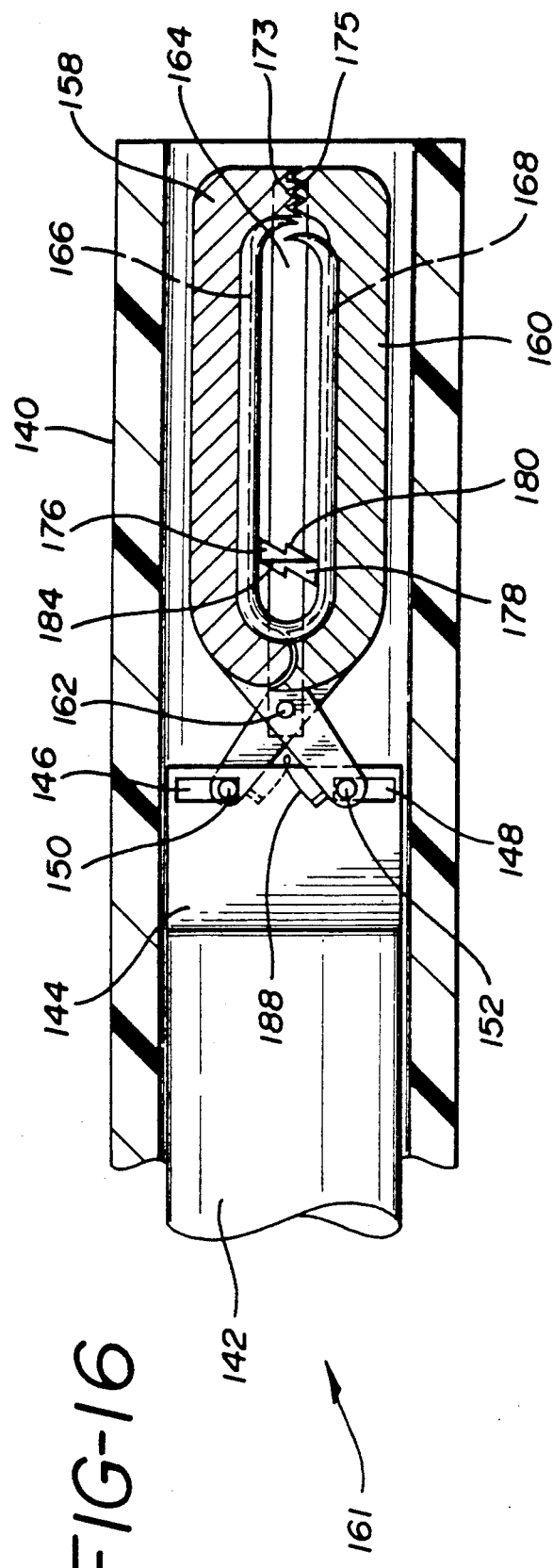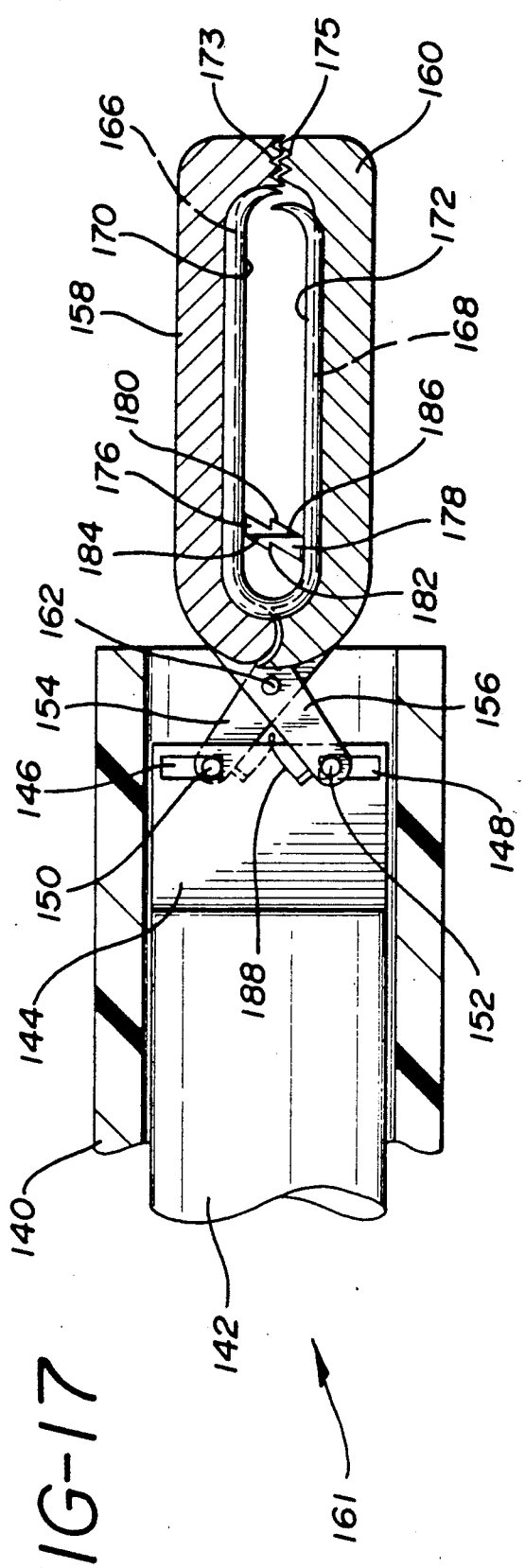

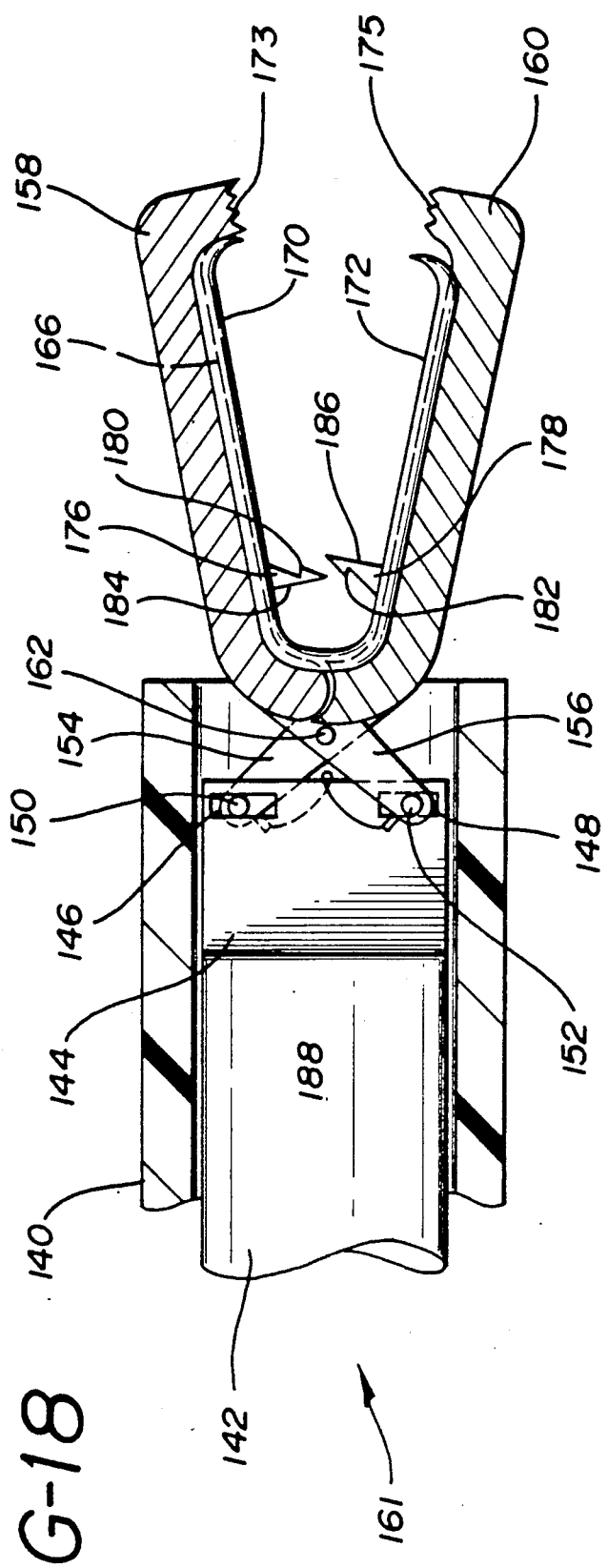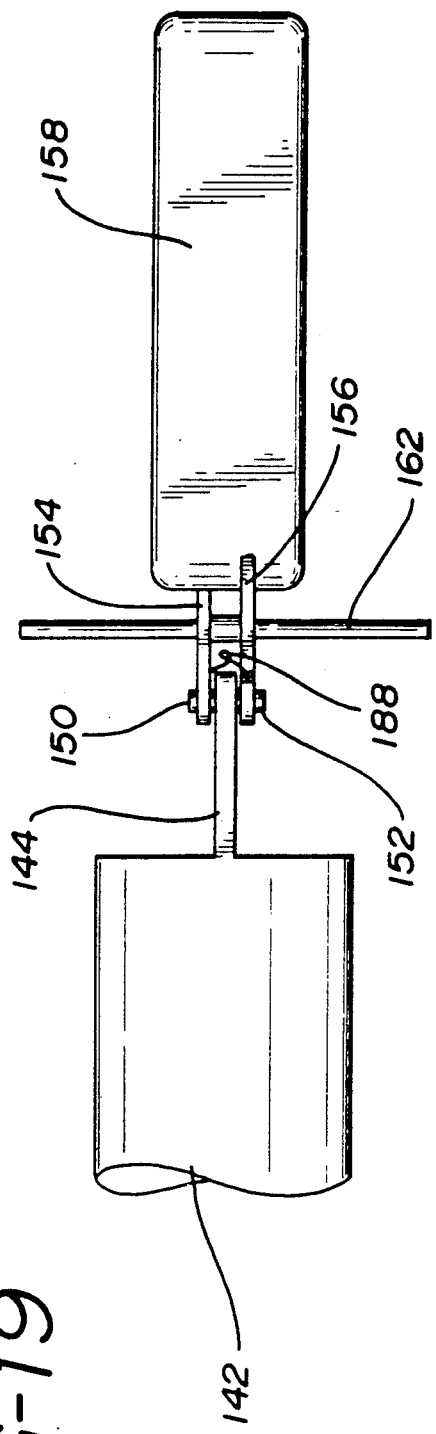
FIG-18
FIG-19

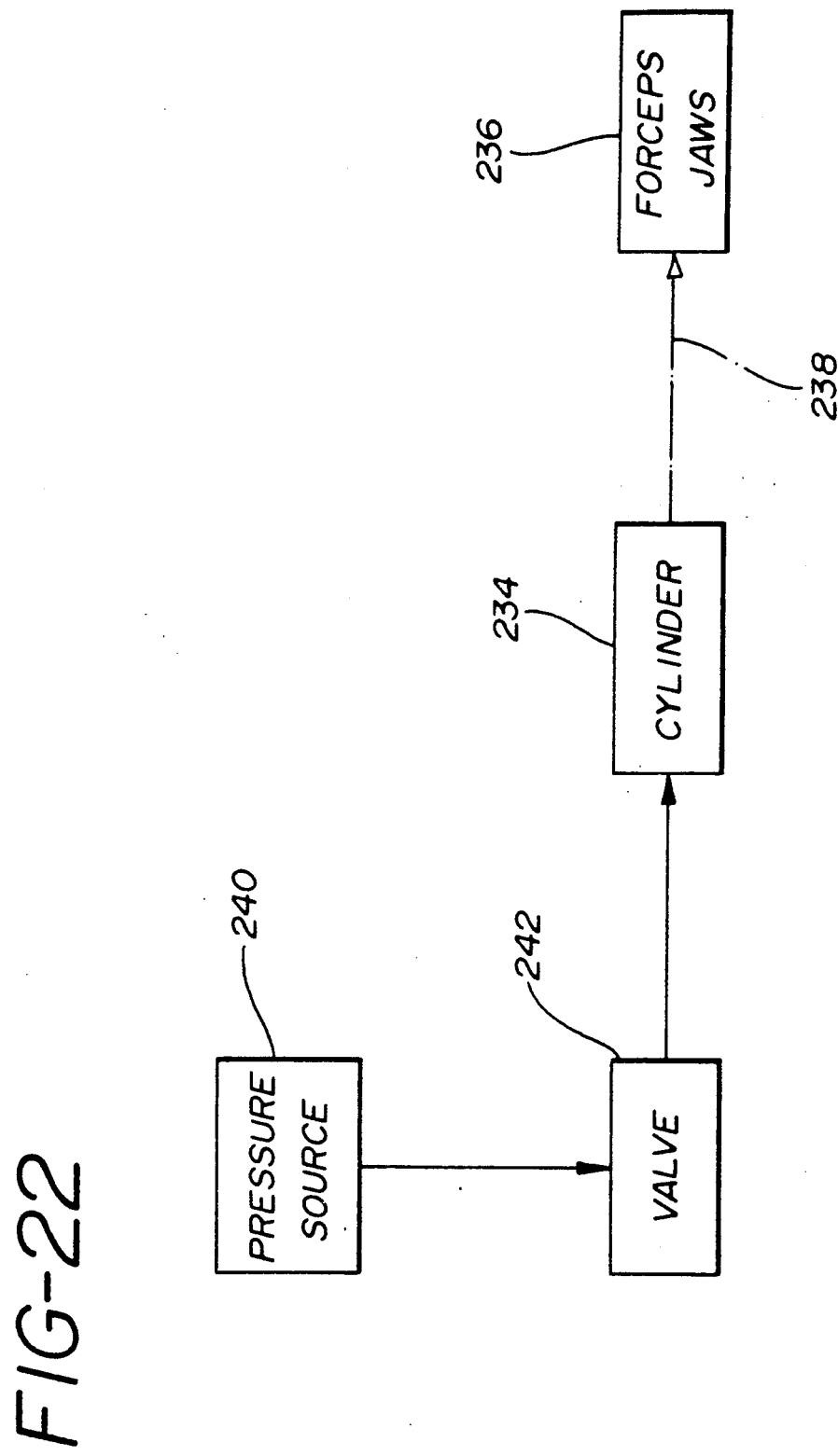

ENDOSCOPIC STAPLING DEVICE AND METHOD

CROSS-REFERENCE TO RELATED APPLICATION

This application is a continuation-in-part of commonly owned application Ser. No. 456,960 filed Dec. 26, 1989, now U.S. Pat. No. 5,015,249.

BACKGROUND OF THE INVENTION

This invention relates to an endoscopic stapling device. More particularly, this invention relates to a device usable with an endoscope for performing a stapling operation on a patient's internal body tissues at a surgical site not visible to the unaided eye. This invention also relates to a surgical procedure utilizing an endoscope. The invention also involves a surgical staple and an associated staple holder or package.

Conventional surgical techniques for repairing tissue injuries such as hernias and perforated ulcers, for closing other openings in internal body tissues and for ligating tubular body organs such as sperm ducts and Fallopian tubes, generally require that an extensive incision be made in the patient's abdominal wall. Such an operation is generally traumatic to the patient, involves considerable surgeon time and requires a relatively lengthy convalescence. This is the case even though only one or a small number of sutures is required to repair the injury or tie off the vessel.

OBJECTS OF THE INVENTION

An object of the present invention is to provide a surgical procedure for closing openings internal to a patient's body, which is less invasive than conventional surgical closure methods.

Another object of the present invention is to provide such a surgical procedure which is quicker than conventional surgical procedures and which reduces the typical postoperative convalescence period.

A related object of the present invention is to provide an improved surgical closure procedure using an endoscope.

Another object of the present invention is to provide a stapling device usable with an endoscope.

An associated object of the present invention is to provide an endoscopic stapling device.

Another, more particular, object of the present invention is to provide a staple usable with such an endoscopic stapling device.

A further particular object of the present invention is to provide a staple package for use with such an endoscopic stapling device.

SUMMARY OF THE INVENTION

A surgical instrument in accordance with the present invention comprises an elongate flexible forceps member having a diameter sufficiently small so that the forceps member is slidably insertable into a biopsy channel extending longitudinally through a flexible tubular endoscope member, the forceps member being provided at a distal end with a pair of forceps jaws each formed on an inwardly facing surface with a longitudinally extending groove. A staple having a spring bias construction tending to force the staple into an opened configuration is disposed in a closed prefiring configuration between the jaws and has a pair of legs each disposed in the closed prefiring configuration in a respective one of the grooves in the forceps jaws. The staple is provided with locking elements for locking the staple in a closed postfiring configuration.

Pursuant to another feature of the present invention, the staple has a pair of legs joined by a bight portion, the means for locking includes a pair of interlocking hook elements on the legs. Preferably, the interlocking hook elements each includes a hook side and a smooth side, the smooth sides of the interlocking hook elements engaging one another and the hook sides of the interlocking hook elements facing away from one another in the closed prefiring configuration of the staple. The interlocking hook elements are disposed either at the distal ends of the legs or proximally of the distal ends of the legs, and specifically proximately to the bight portion of the staple.

Another surgical instrument in accordance with the present invention comprises an elongate flexible forceps member having a diameter sufficiently small so that the forceps member is slidably insertable into a biopsy channel extending longitudinally through a flexible tubular endoscope member, the forceps member being provided at a distal end with a pair of forceps jaws each formed at a distal end with an inwardly turned portion in turn formed with means for gripping internal body tissues. A staple is disposed in a closed prefiring configuration between the jaws Mounting elements are formed on the jaws for holding the staple between the jaws, while a mechanism is provided for opening the staple upon an opening of the jaws. In addition, a device is provided for locking the staple in a closed postfiring configuration.

Pursuant to further features of the present invention, the mounting elements include grooves formed on inwardly faces sides of the jaws, the staple having legs seated in the grooves, the opening mechanism includes a spring bias construction of the staple tending to force the staple into an opened configuration, and the locking device includes a pair of interlocking hook elements on the legs. As discussed above, the interlocking hook elements each preferably includes a hook side and a smooth side, the smooth sides of the interlocking hook elements engaging one another and the hook sides of the interlocking hook elements facing away from one another in the closed prefiring configuration. The interlocking hook elements are disposed at the distal ends of the legs or proximately to the bight portion of the staple.

A method for stapling internal body tissues comprises, in accordance with the present invention, the step of providing a staple having a spring bias construction tending to force the staple into an opened configuration. The staple has a pair of legs connected to one another by a bight portion and locking elements for maintaining the staple in a closed postfiring configuration. The locking elements include a first locking element on one of the legs and a second locking element on another of the legs, the first locking element having a hook on a distal side and a smooth face on a proximal side, the second locking element having a hook on a proximal side and a smooth face on a distal side. The method further comprises the step of holding the staple in a closed prefiring configuration inside the distal end of an endoscope member so that the smooth face of the first locking element is in contact with the smooth face of the second locking element. In a subsequent step, the staple is shifted in a distal direction to eject the staple from the endoscope member. The staple is then opened and the distal ends of the legs of the staple are inserted into the internal body tissues to be stapled. In another step, the staple is closed so that the hook of the first locking element engages the hook of the second locking element.

Another method for performing a surgical operation on internal body tissues of a patient comprises, in accordance with the present invention, the steps of (a) inserting a tubular endoscope member through an aperture in the patient's body, (b) using the endoscope to visually locate the internal body tissues inside the patient's body, and (c) upon locating the surgical site, pushing an elongate flexible forceps member in a distal direction through a biopsy channel in the tubular endoscope member to eject a staple stored in a closed configuration between jaws of the forceps member inside the channel at a distal end of the tubular endoscope member. Upon ejection of the staple from the channel, the jaws of the forceps member are opened and the staple is changed from the closed configuration to an opened configuration. Subsequently, the forceps member is pushed further in the distal direction to move the opened staple and the jaws towards the internal body tissues. The jaws are then closed to grip the internal body tissues and to close the staple in the body tissues and the staple is locked in a closed postfiring configuration in the internal body tissues. Upon closure of the staple, the forceps member is opened to release the internal body tissues. Upon such opening of the forceps member, the forceps member is retracted into the endoscope biopsy channel and the tubular endoscope member is withdrawn from the patient's body though the aperture.

BRIEF DESCRIPTION OF THE DRAWING

FIGS. 4A-4I are partially schematic, partial perspective views, taken from the side and on a reduced scale, of an endoscopic stapling device in accordance with the present invention, showing successive stages in the application of a surgical staple to internal body tissues.

FIG. 9 is a side elevational view of another staple usable in an endoscopic stapling device in accordance with the present invention, showing the staple in an opened configuration.

FIG. 10 is a side elevational view of the staple of FIG. 9 in a closed, postfiring configuration.

FIG. 11 is a side elevational view of the staple of FIGS. 9 and 10, showing the staple in a closed, prefiring configuration.

FIG. 12 is a rear perspective view of the staple of FIGS. 9-11, showing the staple in the closed, prefiring configuration.

FIG. 16 is a partial longitudinal cross-sectional view of another endoscopic stapling device in accordance with the present invention, showing a forceps member and a staple in a closed prefiring configuration between jaws of the forceps member.

FIG. 17 is a partial longitudinal cross-sectional view of the endoscopic stapling device of FIG. 16, showing the forceps member in an extended position relative to a tubular sheath.

FIG. 18 is a partial longitudinal cross-sectional view of the endoscopic stapling device of FIGS. 16 and 17, showing the forceps member and the staple in an opened configuration.

FIG. 19 is a top view of the forceps member of FIGS. 16, 17 and 18.

FIG. 22 is a block diagram of yet another endoscopic stapling device in accordance with the present invention.

DETAILED DESCRIPTION

Figure 1:
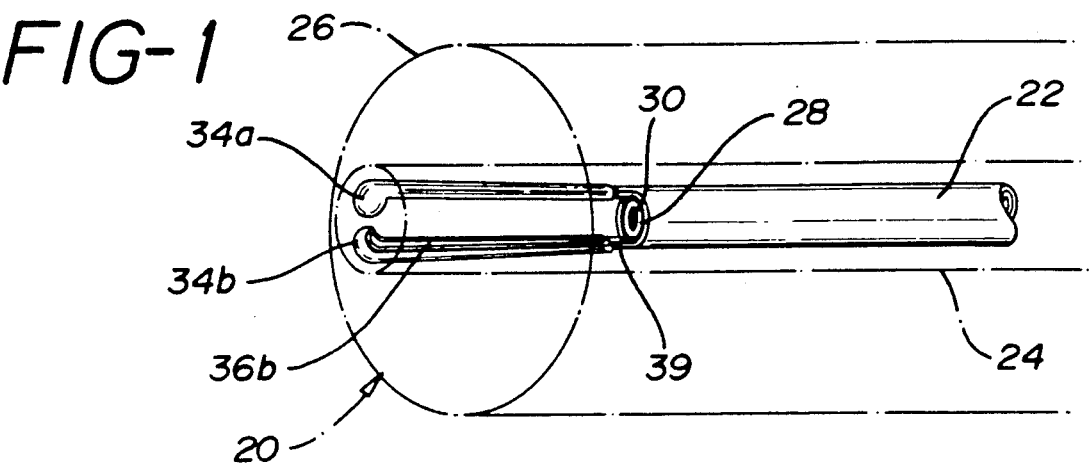
FIG. 1 is a partial perspective view, taken from the side, of an endoscopic stapling device in accordance with the present invention, showing the device in a prefiring configuration without a loaded staple.
Figure 2:
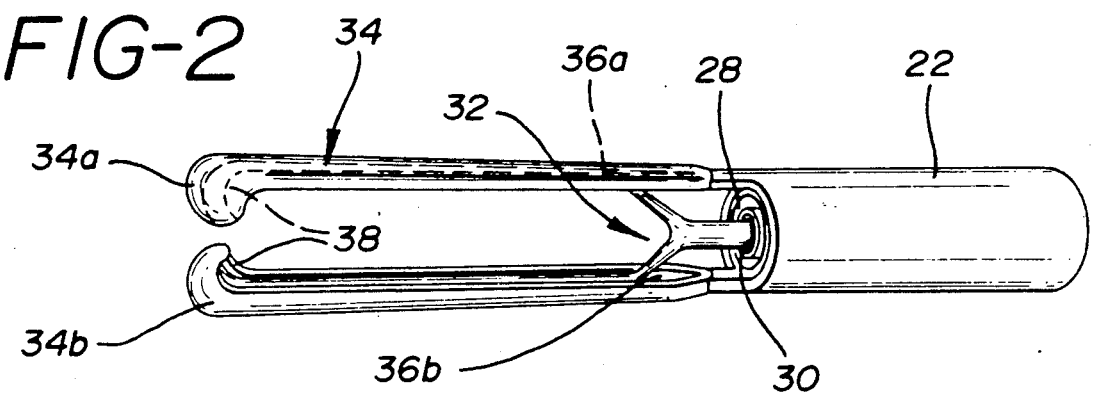
FIG. 2 is a partial perspective view, similar to FIG. 1, showing the endoscopic stapling device in the prefiring configuration with a loaded staple in a closed configuration.

As illustrated in FIGS. 1 and 2, an endoscopic stapling device 20 comprises an outer elongate flexible tubular member 22 having a diameter sufficiently small so that the tubular member is slidably insertable into a biopsy channel 24 extending longitudinally through a flexible tubular endoscope member 26. Endoscopic stapling device 20 further comprises an inner elongate flexible tubular member 28 slidably disposed inside tubular member 22 and an elongate flexible rod member 30 slidably disposed inside inner tubular member 28. In the prefiring configuration of FIG. 2, a staple 32 is disposed in a closed configuration at least partially inside inner tubular member 28 distally of a distal end of rod member 30.

Figure 3:
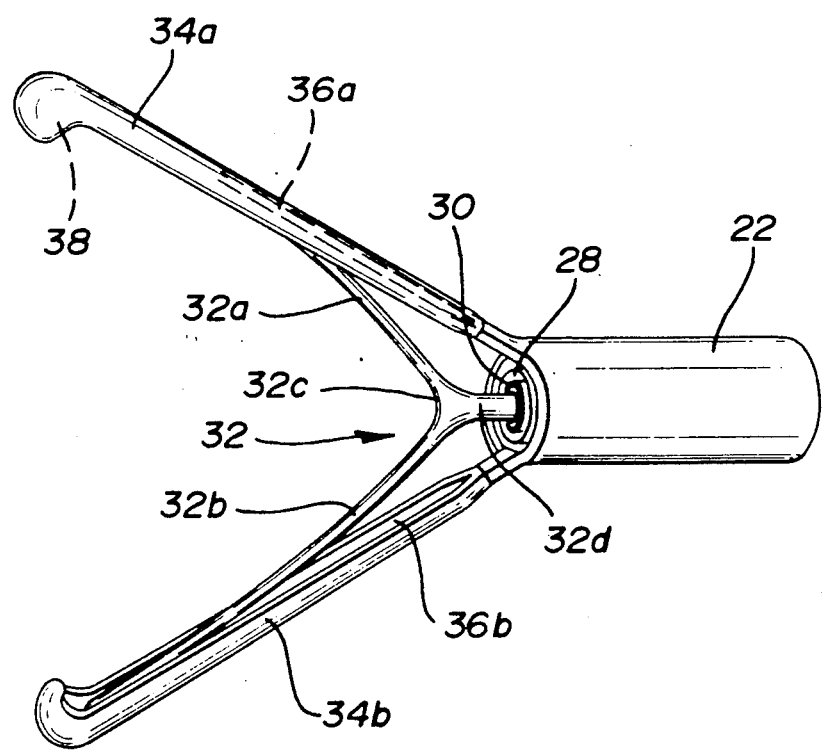
FIG. 3 is a partial perspective view, taken from the side, of the endoscopic stapling device of FIGS. 1 and 2, showing the device in an initial firing stage with an opened staple.

Outer tubular member 22 is provided at a distal end with a forceps 34 including a pair of spring loaded jaws 34a and 34b. As shown in FIGS. 2 and 3, staple 32 includes a pair of legs 32a and 32b seated in the prefiring configuration of the endoscopic stapling device 20 in grooves 36a and 36b provided on inwardly facing surfaces of forceps jaws 34a and 34b. As described hereinafter with reference to FIGS. 4A–4I, jaws 34a and 34b serve to open staple 32 upon an ejection thereof from inner tubular member 28 by a distally directed motion of rod member 30. Jaws 34a and 34b are releasably connected to staple legs 32a and 32b so that staple 32 becomes detached from forceps 34 upon the attainment of a predetermined angular displacement between jaws 34a and 34b. More particularly, the free ends of staple legs 32a and 32b are held in the prefiring configuration of the endoscopic stapling device in cup-shaped recesses 38 formed at the free ends of jaws 34a and 34b.

Staple 32 further includes a bight portion 32c joining staple legs 32a and 32b to one another and to a planar projection 32d extending away from bight portion 32c in a direction opposite legs 32a and 32b. In the staple loaded configuration of FIG. 2, projection 32d is received in a cross-sectionally rectangular recess or opening 39 at the distal end of rod member 30.

It is to be noted that projection 32d and recess 39 may have any of several different geometric shapes. In particular, other polygonal cross-sections can be used.

As shown in FIGS. 4A through 4I, endoscopic stapling device 20 includes an assembly 40 at its proximal end for enabling the operation of the device by a surgeon during an operation. Assembly 40 includes a housing or casing member 42 mountable to endoscope 26 at a proximal end thereof. Projecting from casing 42 are a plurality of handles or knobs 44, 46 and 48 which are mechanically connected to outer tubular member 22, rod member 30 and inner tubular member 28, respectively, for enabling the sliding of those members along biopsy channel 24 by a surgeon or other authorized operator. FIGS. 4A through 4I show the positions of handles 44, 46 and 48 corresponding to the operative configurations of outer tubular member 22, rod member 30, inner tubular member 28, and staple 32 shown in the respective drawing figures.

Figure 4A:
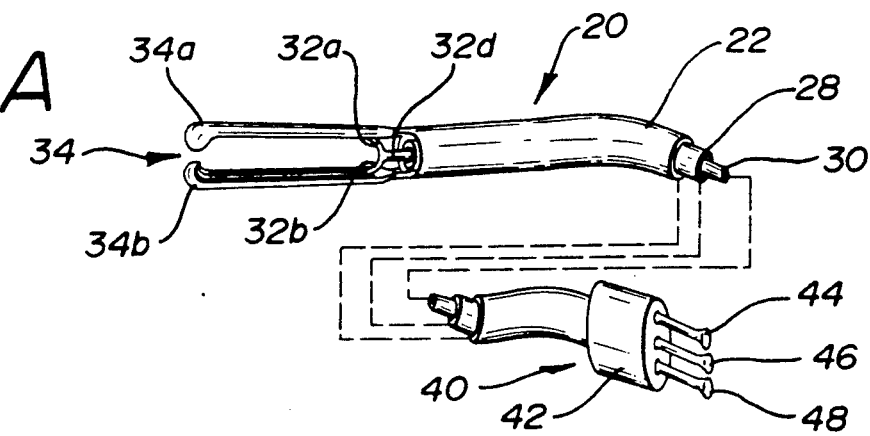
Figure 4B:
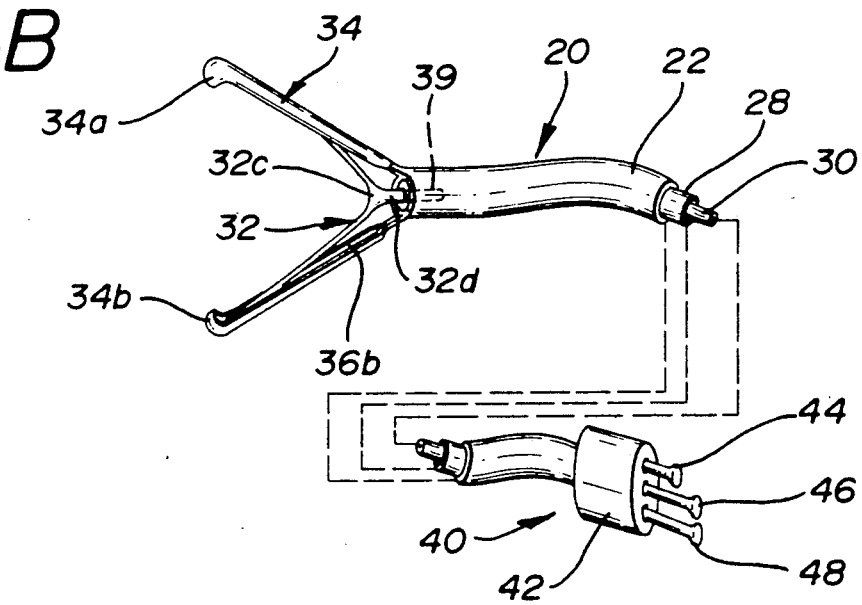

FIGS. 4A and 4B are similar to FIGS. 2 and 3. FIG. 4A shows endoscopic stapling device 20 in a prefiring configuration in which outer tubular member 22, inner tubular member 28, rod 30 and staple 32 are all located in biopsy channel 24 of endoscope 26. More specifically, staple 32 is disposed in a closed prefiring configuration distally of rod member 30 and inside tubular member 28 at the distal end thereof. Endoscope 26 has already been inserted through an aperture (not illustrated) in a patient's body (not shown) and has been used to visually locate in the patient's body the internal body tissues upon which a stapling operation is to be performed. The internal body tissues may be a vessel or duct which needs to be closed or perhaps an opening in the stomach wall.

Figure 4C:
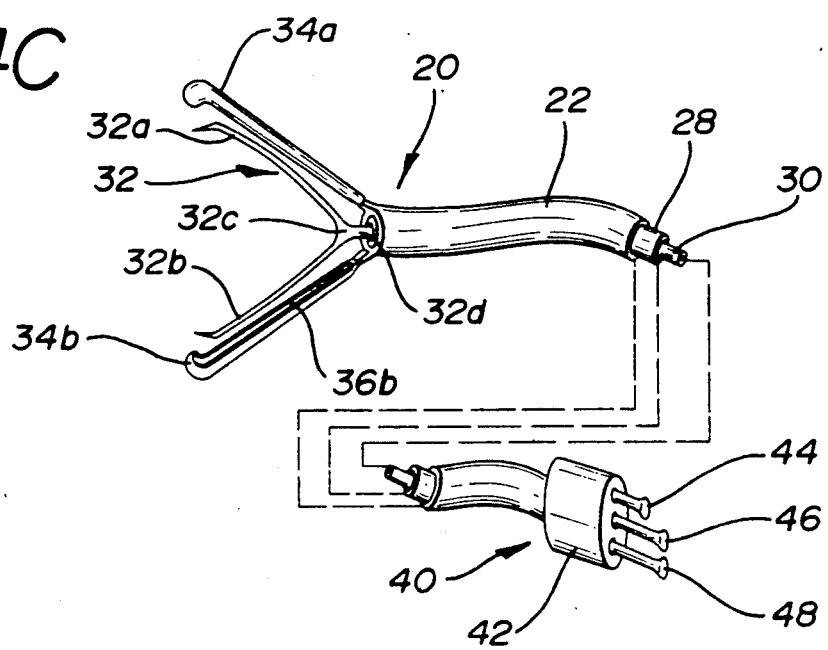

Upon the locating of the surgical site, tubular outer member 22 and rod member 30 are pushed in the distal direction through biopsy channel 24 to eject staple 32 from tubular member 28. During this distal motion, jaws 34a and 34b pivot away from one another and pull apart staple legs 32a and 32b, as shown in FIG. 4B. Upon a further outward pivoting of jaws 34a and 34b, the free ends of legs 32a and 32b slip out from recesses 38 at the distal ends of grooves 36a and 36b. Staple 32 is now in a released, opened configuration, as depicted in FIG. 4C.

In the next step of a surgical procedure using endoscopic stapling device 20, rod member 30 is pushed further in the distal direction to move opened staple 32 towards internal body tissues 50 having an opening 52 previously detected through the optical pathway (not illustrated) of endoscope 26. FIG. 4D shows staple 32 substantially embedded in the body tissues 50 in a region about opening 52.

Upon the embedding of opened staple 32 in internal body tissues 50, inner tubular member 28 is pushed in the distal direction to engage staple legs 32a and 32b and thereby close the staple about opening 52. The distal motion of inner tubular member 28 relative to rod member 30 and staple 32 bends legs 32a and 32b about bight portion 32c, causing staple 32 to assume a closed, tissue-clamping configuration shown in FIG. 4E.

In a subsequent step shown in FIG. 4F, inner tubular member 28 is retracted into biopsy channel 24. In an optional step depicted in FIG. 4G, rod member 30 may be moved even further in the distal direction to push staple 32 further into tissues 50. This step serves to limit the extent that the staple projects from tissues 50.

Upon a satisfactory disposition of staple 32 in tissues 50, whereby opening 52 is stapled closed, rod member 30 is retracted into inner tubular member 28 (FIG. 4H). Outer tubular member 22 is then moved in the proximal direction into biopsy channel 24, jaws 34a and 34b being pivoted towards one another during the proximally directed stroke of outer tubular member 22. The pivoting of jaws 34a and 34b is effectuated by a camming action when the jaws slide past the rim or lip at the distal end of biopsy channel 24.

Upon the completion of the stapling operation, outer tubular member 22, inner tubular member 28 and rod member 30 are all disposed in biopsy channel 24, so that the distal ends of those members do not extend beyond the distal end of the channel. The entire endoscopic instrument is then withdrawn from the patient's body through the aperture through which it was introduced. That aperture may take the form of a natural body opening. Alternatively, the endoscope introduction aperture may be formed through the use of a trocar. Such a procedure can be followed, for example, to repair a hernia through a small opening in the abdominal wall.

Figure 5:
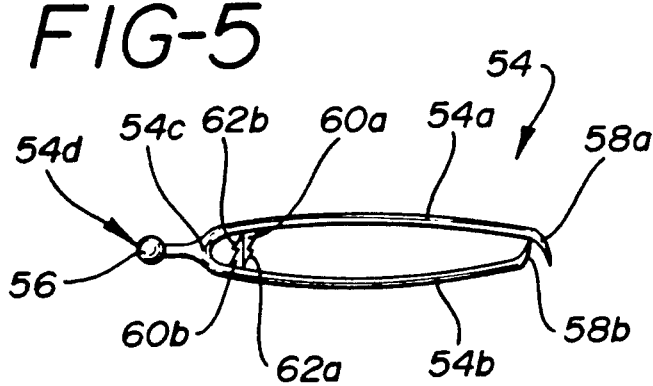
FIG. 5 is a side elevational view, on an enlarged scale, of a staple for use in an endoscopic stapling device in accordance with the present invention, showing the staple in a prefiring closed configuration.
Figure 6:
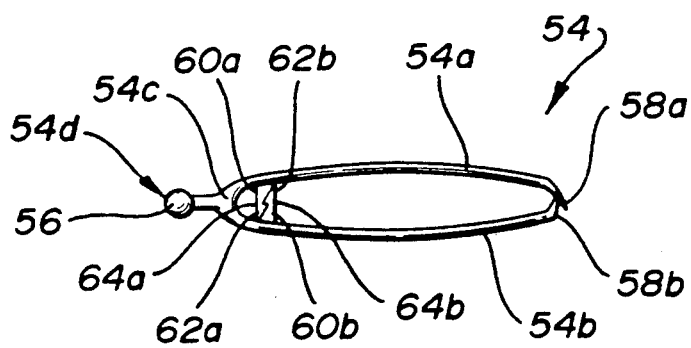
FIG. 6 is a side elevational view of the staple of FIG. 5, showing the staple in a closed, postfiring configuration.

As illustrated in FIGS. 5 and 6, a staple 54 for an endoscopic stapling device in accordance with the present invention includes a pair of legs 54a and 54b joined by a bight section 54c and provided on a side of the bight section opposite the legs with a projection 54d terminating in a knob or ball 56. Each leg 54a and 54b is provided at a free end with a respective inwardly turned foot 58a and 58b. In addition, on their inward facing sides, legs 54a and 54b are provided towards the proximal end of the staple with interlocking finger elements 60a and 60b having barbs or hooks 62a and 62b which cooperate with one another to lock the staple in a closed configuration at the end of a stapling operation.

Staple 54 is spring biased, by virtue of the inherent structural characteristics of its preferably metallic material, towards an opened (legs spread) configuration. The material and dimensions of staple 54 are selected so that the staple is sufficiently flexible to be temporarily distorted into the prefiring configuration shown in FIG. 5. In that configuration, legs 54a and 54b are longitudinally shifted relative to one another and interlocking finger elements 60a and 60b releasably engage each other along planar faces 64a and 64b.

Figure 7A:
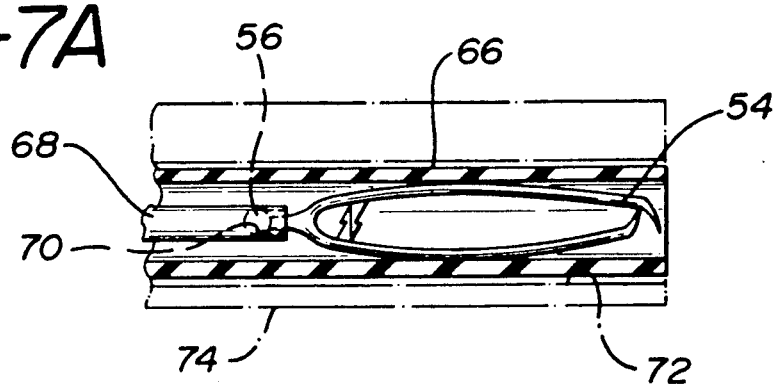
FIGS. 7A-7F are partially schematic, partial perspective views, taken from the side and on a reduced scale, of an endoscopic stapling device in accordance with the present invention, showing successive steps in the application of the surgical staple of FIGS. 5 and 6 to internal body tissues.

As illustrated in FIG. 7A, staple 54 is disposed in its prefiring configuration inside the distal end of an elongate flexible tubular member 66 distally of an elongate flexible rod member 68 itself slidably inserted in tubular member 66. Staple 54 is releasably attached to rod member 68 by a ball and socket connection comprising knob 56 and a corresponding recess 70 at the distal end of rod 68.

Figure 7B:
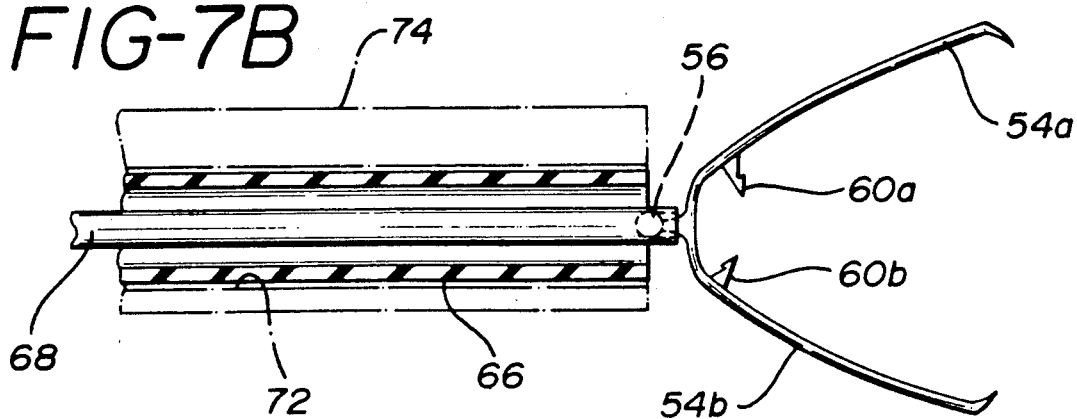
Figure 7C:
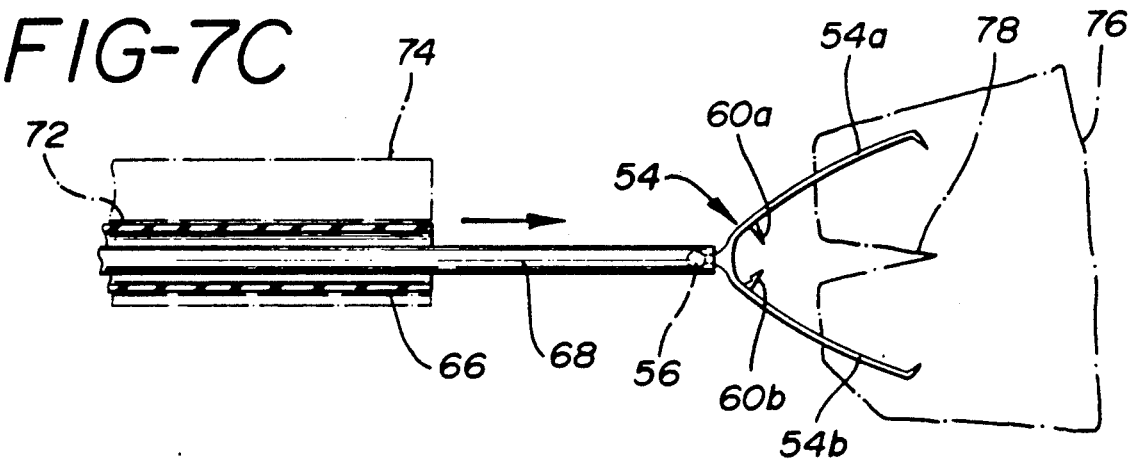

Tubular member 66 has a diameter sufficiently small so that it is slidably insertable into a biopsy channel 72 extending longitudinally through a flexible tubular endoscope member 74. Upon the insertion of the endoscope, with tubular member 66, rod member 68 and staple 54 disposed in the endoscope's biopsy channel, into a patient's body and the location, via the fiberoptics of the endoscope, of an internal site requiring a closure, rod member 68 is shifted in a distal direction to eject staple 54 from tubular member 66. The ejected staple automatically assumes an opened configuration illustrated in FIG. 7B. Further distally directed motion of rod member 68 pushes the opened staple 54 into the internal body tissues 76 of the patient, as shown in FIG. 7C.

Figure 7D:
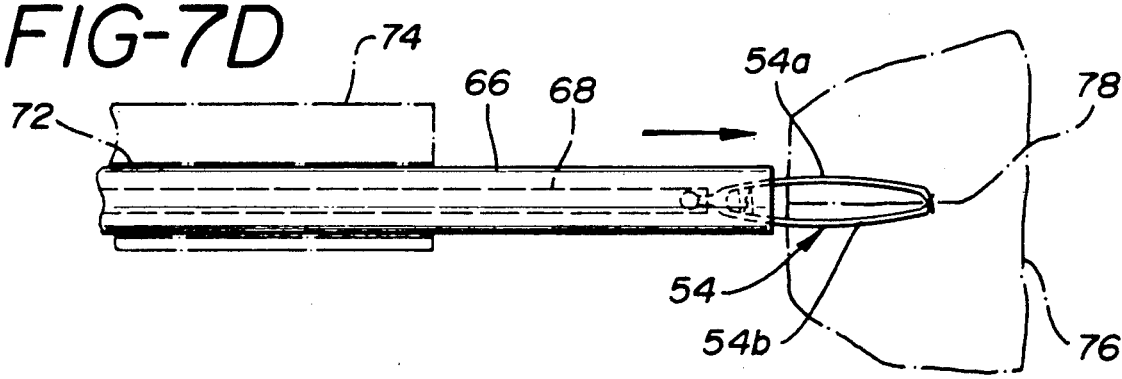
Figure 7E:
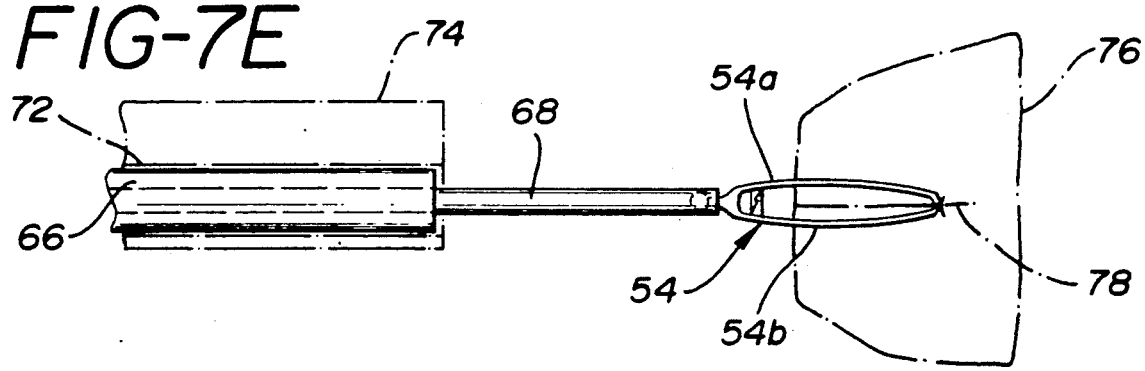
Figure 7F:
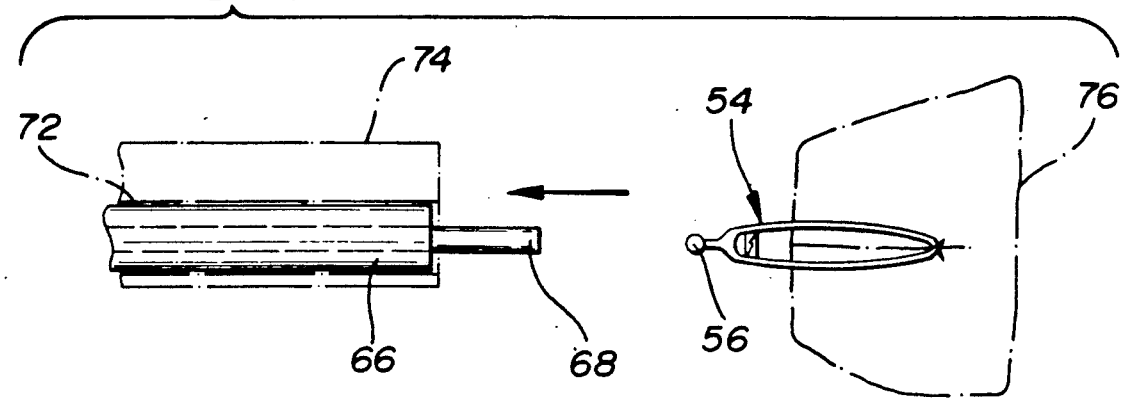

Upon an embedding of staple 54 in body tissues 76 about a cut, tear or other opening 78, tubular member 66 is shifted distally from the endoscope and engages staple legs 54a and 54b to bend them inwardly towards one another in opposition to the internal spring forces of the staple. Upon a sufficient advance of tubular member 66, barbs or hooks 62a and 2b of finger elements 60a and 60b interlock and hold staple legs 54a and 54b in the closed configuration (FIG. 7D). Tubular member 66 is then withdrawn back into the biopsy channel of the endoscope (FIG. 7E). Finally, as depicted in FIG. 7F, rod member 68 is retracted and the endoscope removed from the patient's body.

In an alternative series of steps, rod member 68 is retracted prior to the withdrawal of tubular member 66. In that procedure, tubular member 66 serves to hold staple 54 against the return stroke of rod member 68 and facilitates the removal of knob 56 from recess 70. Usually, however, it is contemplated that the forces holding the ball and socket joint together are smaller than the forces retaining staple 54 in body tissues 76 so that there will be no problem retracting rod member 68 subsequently to the withdrawal of tubular member 66.

As illustrated in FIGS. 8A–8F, another endoscopic stapling device 80 similar to the device of FIGS. 7A–7F includes an outer elongate flexible tubular member 82 having a diameter sufficiently small so that the tubular member is slidably insertable into a biopsy channel 84 extending longitudinally through a flexible tubular endoscope member 86. Endoscopic stapling device 80 further comprises an inner elongate flexible tubular member 88 slidably disposed inside tubular member 82 and an elongate flexible rod member 90 slidably disposed inside inner tubular member 88. In the prefiring configuration of FIG. 8A, a staple 91 (similar to staple 54) is disposed in a closed configuration at least partially inside inner tubular member 88 distally of a distal end of rod member 90. Staple 91 is releasably attached to rod member 90 by a ball and socket connection comprising a knob-like projection 92 on the staple and a corresponding recess 93 at the distal end of rod 90.

Outer tubular member 82 is provided at a distal end with a forceps 94 including a pair of metal jaws 94a and 94b which are spring biased towards a spread-apart state by virtue of their own internal microstructure.

Figure 8A:
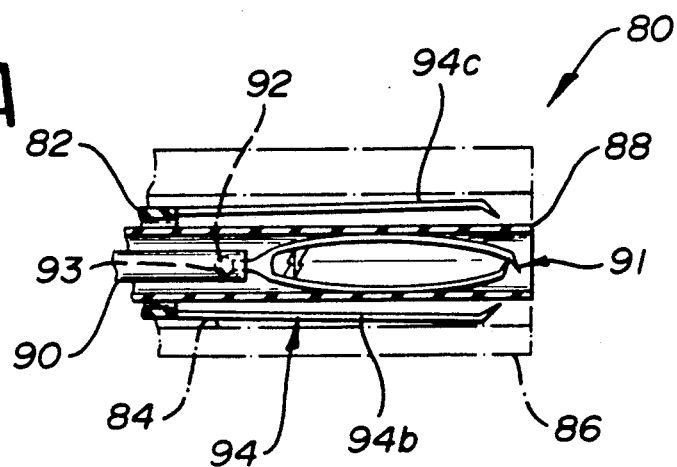
FIGS. 8A-8F are partially schematic, partial perspective views, similar to FIGS. 8A-8F, of another endoscopic stapling device in accordance with the present invention, showing successive stages in the application of the surgical staple of FIGS. 5 and 6 to internal body tissues.

FIG. 8A shows endoscopic stapling device 80 in a prefiring configuration in which outer tubular member 82 including forceps jaws 94a and 94b, inner tubular member 88, rod 90 and staple 91 are all located in biopsy channel 84 of endoscope 86. More specifically, staple 91 is disposed in a closed prefiring configuration (see FIG. 5) distally of rod member 30 and inside tubular member 28 at the distal end thereof.

Figure 8B:
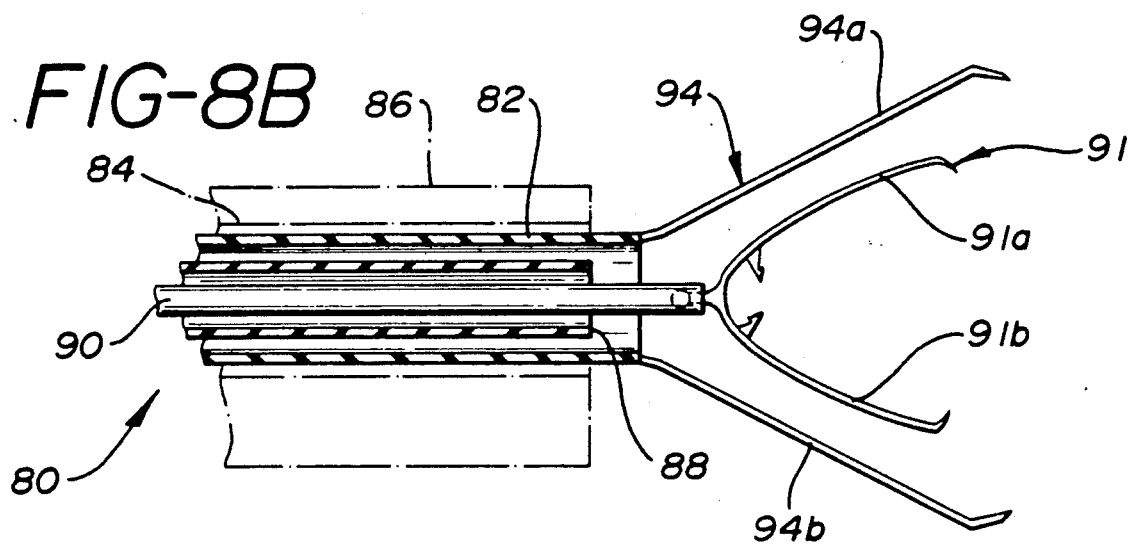
Figure 8C:
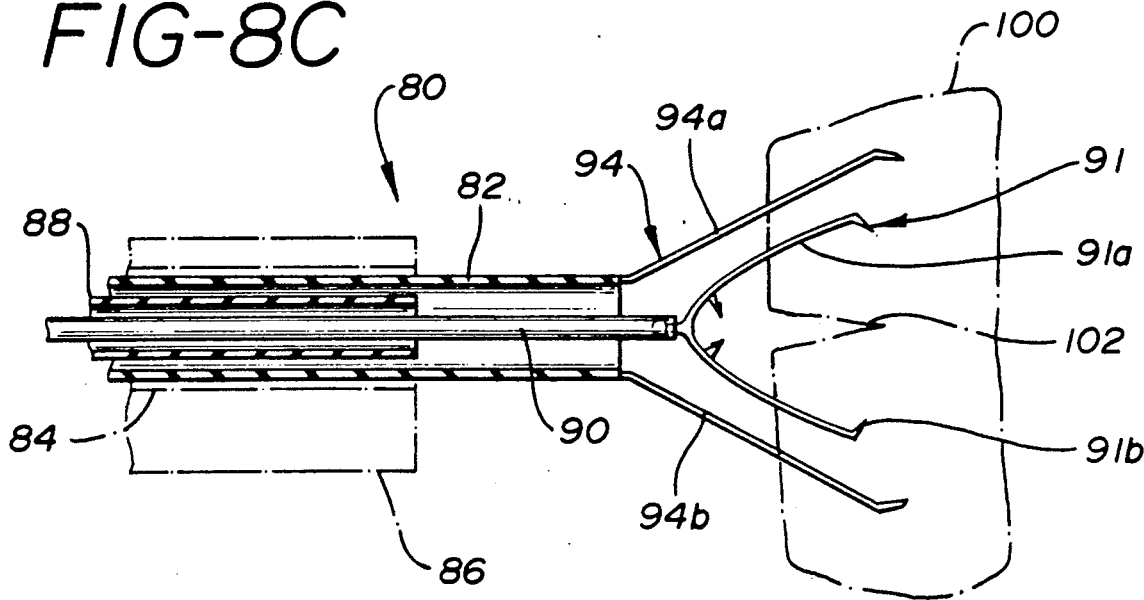

Endoscope 86 is inserted through an aperture (not illustrated) in a patient's body (not shown) and is used to visually locate in the patient's body the internal body tissues upon which a stapling operation is to be performed. Upon the locating of the surgical site, tubular outer member 82 and rod member 90 are pushed in the distal direction through biopsy channel 84 to open forceps jaws 94a and 94b and to eject staple 91 from tubular member 88, as depicted in FIG. 8B.

In the next step of a surgical procedure using endoscopic stapling device 80, outer tubular member 82 and rod member 90 are pushed further in the distal direction to move opened staple 91 towards internal body tissues 100 having an opening 102 previously detected through the optical pathway (not illustrated) of endoscope 86. FIG. 4C shows forceps jaws 94a and 94b and staple 91 substantially embedded in the body tissues 100 in a region about opening 102.

Figure 8D:
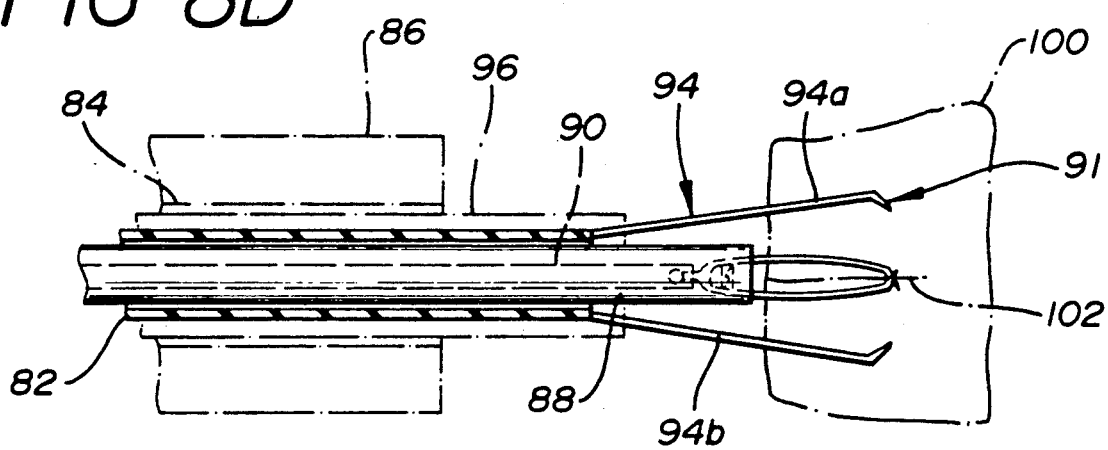
Figure 8E:
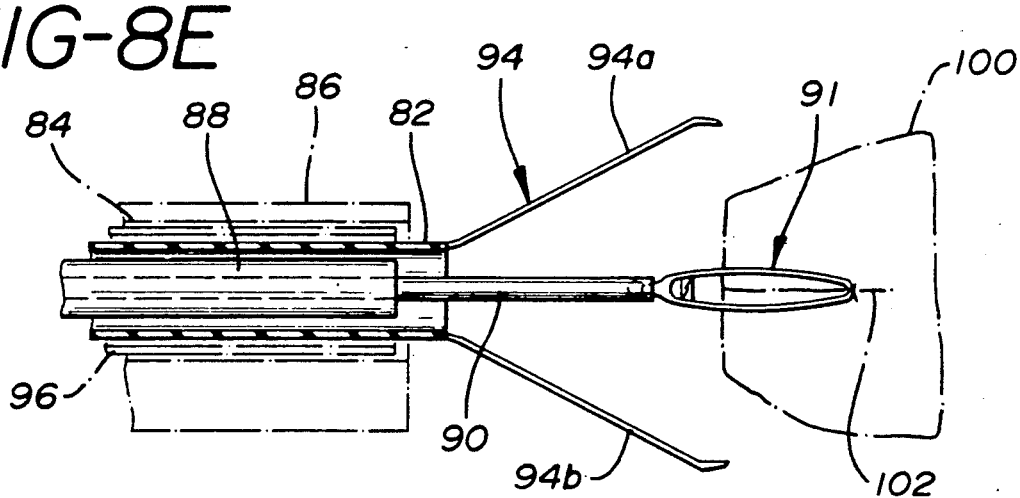
Figure 8F:
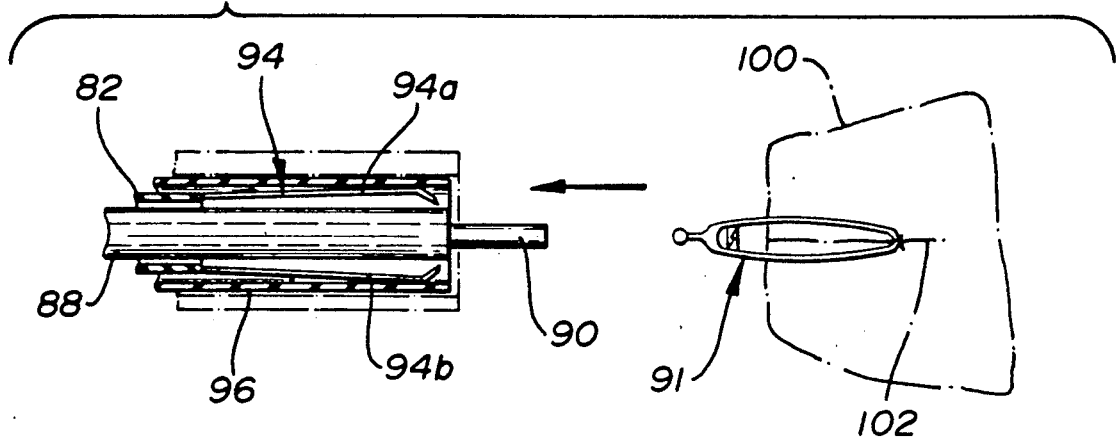

Upon the embedding of opened staple 91 in internal body tissues 100, inner tubular member 88 is pushed in the distal direction to engage staple legs 91a and 91b and thereby close the staple about opening 102. Simultaneously, as illustrated in FIG. 8D, an additional outer tubular member 96 slidably disposed in biopsy channel 84 around tubular member 82 is shifted distally to engage forceps jaws 94a and 94b and thereby close the forceps 94 to aid in the closure of opening 102 during the stapling operation.

In a subsequent step shown in FIG. 4E, outermost tubular member 96 and inner tubular member 88 are retracted into biopsy channel 84. In addition, tubular member 82 is moved proximally to withdraw forceps 94 from body tissues 100. During the retraction of outer tubular member 82 into the endoscope's biopsy channel, forceps jaws 94a and 94b pivot towards one another through a camming action when the jaws slide past the rim or lip at the distal end of biopsy channel 84 or past the mouth of outermost tubular member 96. Finally, rod member 90 is retracted into inner tubular member 88 (FIG. 4F) and the entire endoscopic stapling device is then withdrawn from the patient's body through the aperture through which it was introduced.

Another staple 104 usable in an endoscopic stapling device in accordance with the present invention is illustrated in FIGS. 9–12. That staple includes includes a pair of legs 104a and 104b joined by a bight section 104c and provided on a side of the bight section opposite the legs with a projection 104d terminating in a knob or ball 106. Each leg 104a and 104b is provided at a free end with a respective inwardly turned foot 108a and 108b. Foot 108a is formed on an outer, distally facing side with a barb or hook 110a, while foot 108b is provided on an inwardly or proximally facing face with another barb or hook 110b. As illustrated in FIG. 10, hooks 110a and 110b interfit and thereby cooperate with one another to lock the staple in a closed configuration at the end of a stapling operation.

Like legs 54a and 54b of staple 54, legs 104a and 104b of staple 104 are spring biased outwardly. Thus, a force pressing legs 104a and 104b towards one another is required to close staple 104.

FIGS. 11 and 12 show staple 104 in the prefiring closed configuration. The staple legs 104a and 104b are disposed side-by-side. When staple 104 is opened upon ejection from a tubular member pursuant to the invention, legs 104a and 104b spring apart under the action of internal forces (FIG. 9) so that hooks 110a and 110b are aligned with one another.

The staple of FIGS. 9-12 is particularly useful in closing tubular body organs such as blood vessels, sperm ducts, and Fallopian tubes.

Figure 13:
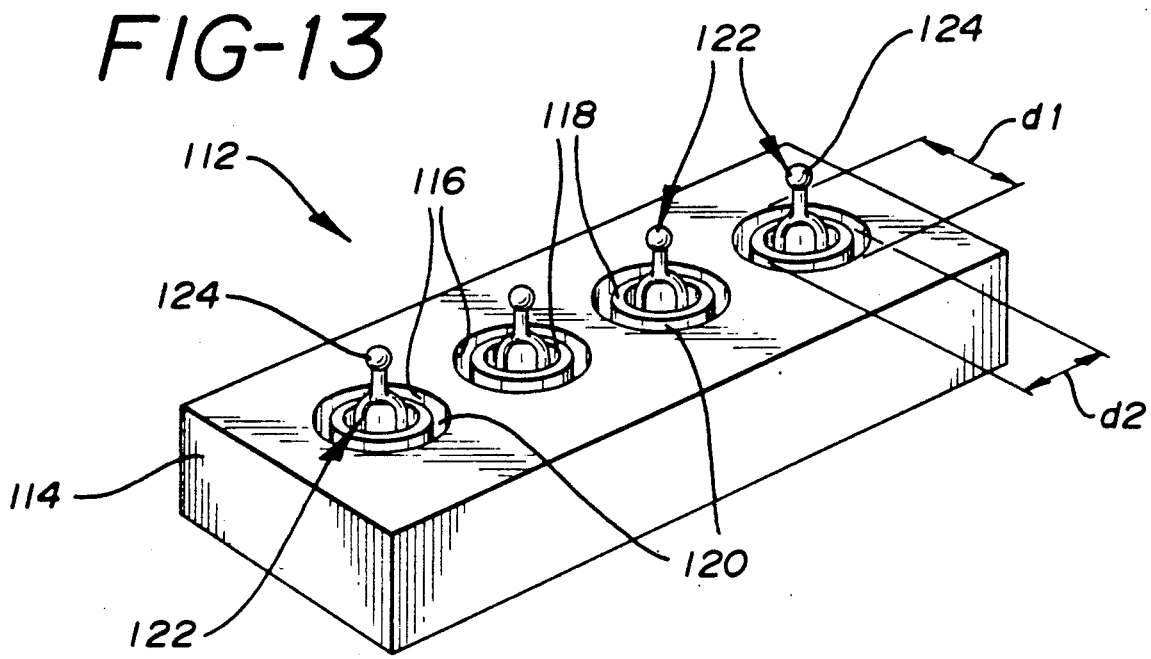
FIG. 13 is an isometric view of a staple package in accordance with the present invention.

As depicted in FIG. 13, a surgical staple package 112 comprises a container 114 provided with a plurality of cylindrical recesses 116 having a common diameter d1. Disposed in each recess 116 is a respective annular sleeve 118. Sleeves 118 have a common outside diameter d2 smaller than diameter d1 of recesses 116, whereby an annular space 120 is formed between each sleeve 118 and the cylindrical wall defining the respective recess 116. A plurality of staples 122 are seated in sleeves 118, each staple 122 being provided with a connector element 124 in the form of a knob, a plate or other cross-sectionally polygonal member for releasably connecting the respective staple to the distal end of a flexible rod member 30, 68, 90 of an endoscopic stapling device. Staples 122, whether in the specific form of staple 32, 54, or 104 or some other form consistent with the principles of the invention, are placed in a prefiring closed configuration in sleeves 118.

Figure 14:
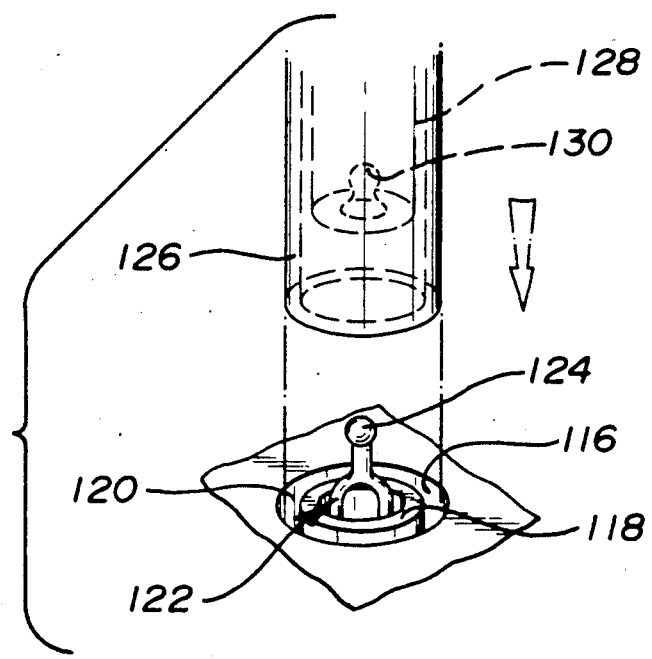
FIGS. 14 and 15 are essentially isometric views of a staple in the package of FIG. 13, showing successive steps in the removal of the staple from the package and the simultaneous loading of the staple into an endoscopic stapling device in accordance with the present invention.
Figure 15:
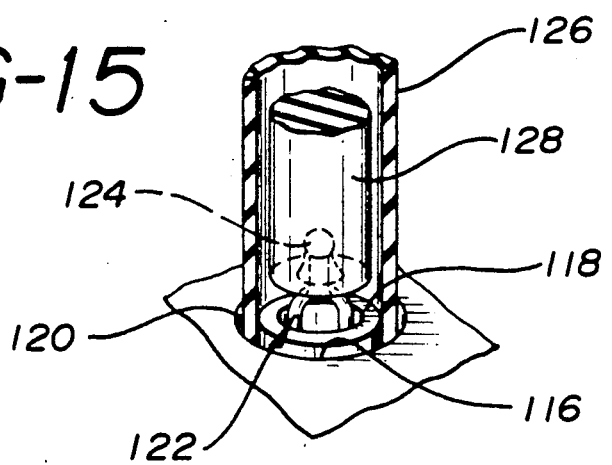

Annular spaces 120 have a width and a diameter sufficiently large so that the annular spaces can each receive the distal end of an inner tubular member 28, 66, 88 of an endoscopic stapling device in accordance with the invention. As illustrated in FIGS. 14 and 15 to load a staple 122 from package 112, the distal end of a flexible tubular member 126 of an endoscopic stapling device in accordance with the invention is inserted into the annular space 120 about the respective staple. Subsequently, a flexible rod member 128 of the endoscopic stapling device is moved distally through tubular member 126 until a recess 130 at the distal end of rod member 128 receives connector element 124, releasably securing the staple 122 to rod member 128. Tubular member 126 is then withdrawn from the annular space 120 and the staple 122 removed from its respective sleeve 118. The entire endoscopic stapling device is then inserted into the biopsy channel of an endoscope. It is to be understood that, should the need arise for more than one staple to close an internal opening, an endoscopic stapling device in accordance with the invention may be removed from the endoscope's biopsy channel and reloaded with another staple while the endoscope remains partially inserted in the patient's body.

As illustrated in FIG. 16, another endoscopic stapling device comprises an elongate flexible outer tubular member 140 having a diameter sufficiently small so that the tubular member is slidably insertable into a biopsy channel extending longitudinally through a flexible tubular endoscope. Slidably inserted inside tubular member 140 is an elongate flexible rod member 142 provided at a distal end with an actuator plate 144 formed at a distal end with a pair of substantially colinear camming apertures or slots 146 and 148. Slots 146 and 148 are traversed by respective pins 150 and 152 connected to respective fingers or levers 154 and 156 of a pair of forceps jaws 158 and 160. Tubular member 140, rod member 142, actuator plate 144, fingers 154 and 156, and jaws 158 and 160 form parts of an elongate flexible forceps member 161 slidably insertable through the biopsy channel of an endoscope for performing stapling operations on internal body tissues of a patient without the necessity of opening the patient's body by means of an extensive incision.

Fingers or levers 154 and 156 are pivotably connected to one another by an elongate transversely oriented pin 162 (see FIG. 19) slidably traversing at its ends a pair of longitudinally extending slots or recesses 164 (one shown in FIG. 16) in tubular member 140. Slots 164 serve to limit the motion of jaws 158 and 160 with respect to tubular member 140 and to guide the jaws in longitudinal shifts along tubular member 140.

Jaws 158 and 160 are formed on inwardly facing surfaces with respective longitudinal grooves 166 and 168 in which legs 170 and 172 of a staple 174 are seated. Staple 174 has a spring bias construction tending to force the staple into an opened configuration. However, prior to the ejection and application of staple 174 during a surgical operation, the staple is maintained between jaws 158 and 160 in a closed prefiring configuration through its seating in grooves 166 and 168.

Distal ends of jaws 158 and 160 are formed with teeth 173 and 175 for gripping or grasping internal body tissues at a surgical site, to pull the tissues together and to maintain them in a bunched state during a stapling operation.

Legs 170 and 172 of staple 174 are provided on inwardly facing sides with a pair of locking elements 176 and 178 formed on distal and proximal sides with respective hooks 180 and 182 and having smooth surfaces 184 and 186 on the opposing sides. In the closed prefiring configuration of FIGS. 16 and 17, smooth surfaces 184 and 186 engage one another and assist in retaining staple 174 in a deformed state.

During a stapling operation, rod member 142 is pushed in a distal direction through tubular member 140, thereby sliding pin 162 along slots 164 until pin 164 contacts the distal ends of the slots. At that time, jaws 158 and 160 have attained their most distal position with respect to tubular member 140. Continued motion of rod member 142 in the distal direction pivots fingers or levers 154 and 156 about pin 162, which remains fixed at the distal end of slots 164, in opposition to a restoring torque exerted on fingers or levers 154 and 156 by a tension spring 188. The pivoting of fingers or levers 154 and 156 also pivots jaws 158 and 160 from the closed configuration of FIGS. 16 and 17 to the opened configuration of FIG. 18. The opening of jaws 158 and 160 allows staple 174 to open under its own internal biasing forces from the closed prefiring configuration of FIGS. 16 and 17 to an opened firing-ready configuration of FIG. 18. As indicated in FIG. 18, legs 170 and 172 of staple 174 shift relative to one another upon an opening of the staple so that locking elements 176 and 178 can lock upon a closing of staple 174 under the pressure exerted by jaws 158 and 160 during a closing thereof. Jaws 158 and 160 are closed by pushing tubular member 140 in the distal direction while maintaining the position of jaws 158 and 160 with respect to an internal surgical site.

Figure 20A:
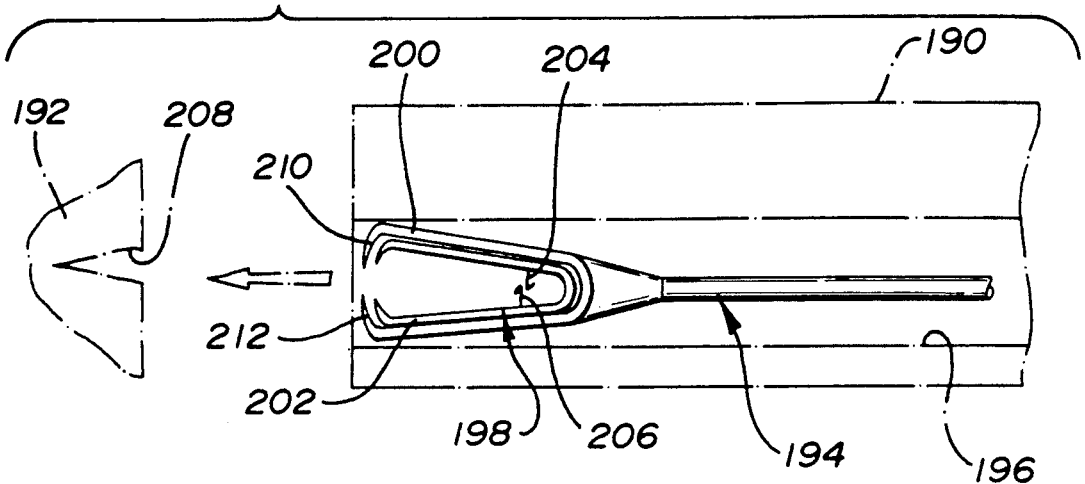
FIGS. 20A through 20D are schematic partial side elevation views showing successive steps in the operation of an endoscopic stapling device like the device of FIGS. 16-19.

As illustrated in FIG. 20A, a stapling operation commences with inserting a tubular endoscope member 190 through an aperture (not illustrated) in a patient's body (not illustrated). The endoscope is used to visually locate internal body tissues 192 inside the patient's body which require a surgical operation. Upon locating the surgical site, a surgeon pushes an elongate flexible forceps member 194 in a distal direction through a biopsy channel 196 in tubular endoscope member 190. The shifting of forceps member 194 results in an ejection from biopsy channel 196 of a staple 198 stored in a closed configuration between jaws 200 and 202 of forceps member 194 inside the biopsy channel at a distal end thereof. Forceps member 194 may take the form of forceps 161 or any similar forceps wherein a staple having an open bias is seated between forceps jaws, preferably but not necessarily in grooves provided in the jaws. Staple 198 preferably takes the form of staple 174 and has locking hook elements 204 and 206 for locking the staple in a closed configuration upon disposition thereof in body tissues 192 on opposite sides of a wound 208.

Figure 20B:
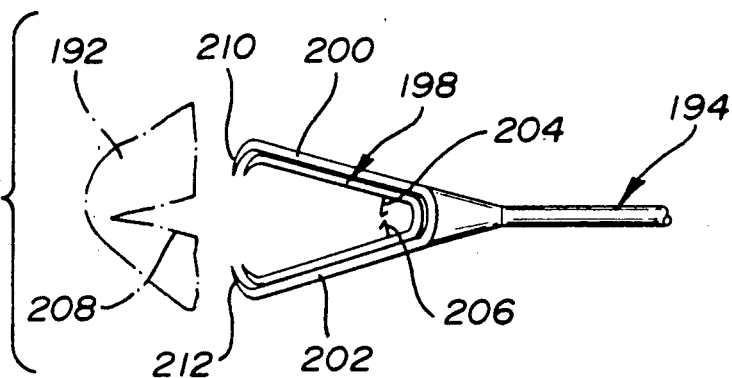
Figure 20C:
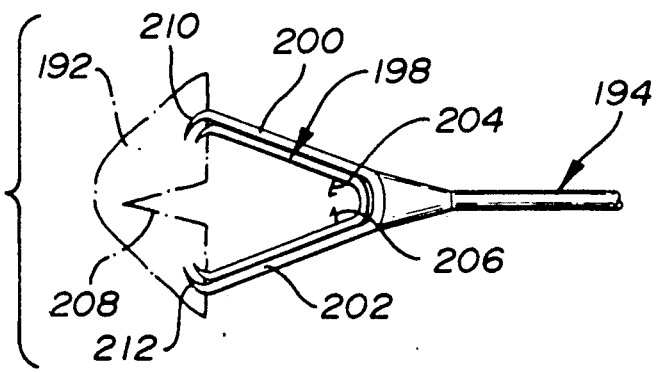
Figure 20D:
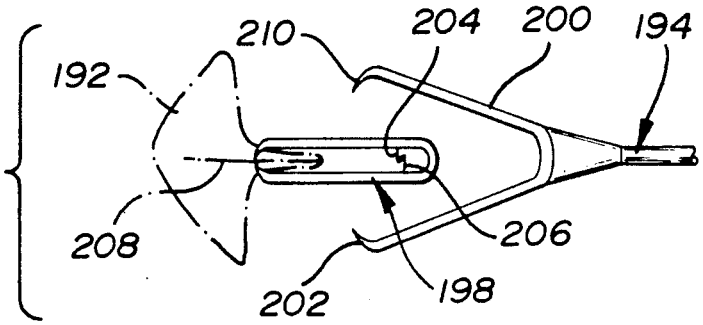
Figure 21A:
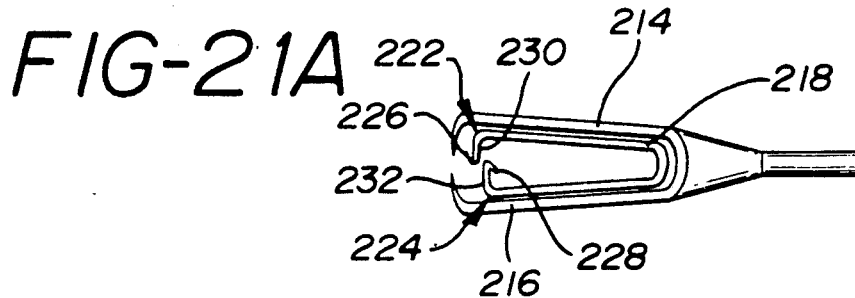
FIGS. 21A through 21D are schematic partial side elevation views showing successive steps in the operation of another endoscopic stapling device like the device of FIGS. 16-19.
Figure 21B:
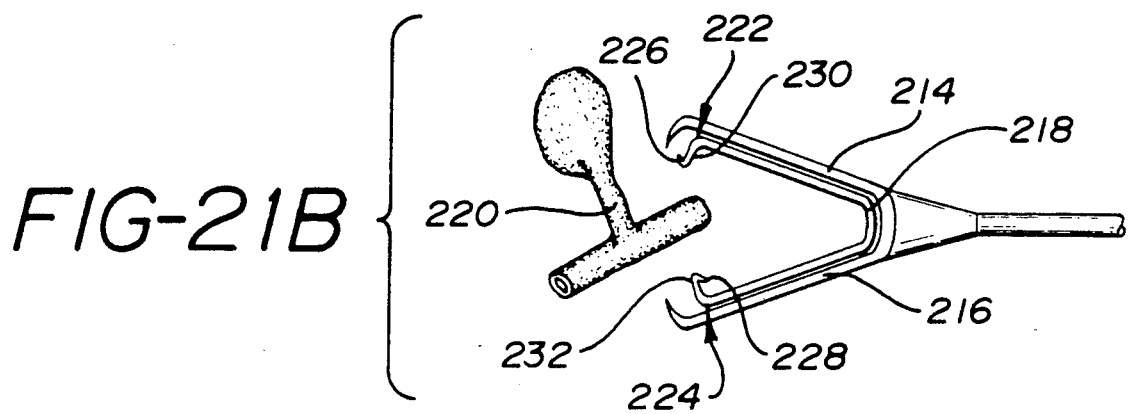
Figure 21C:
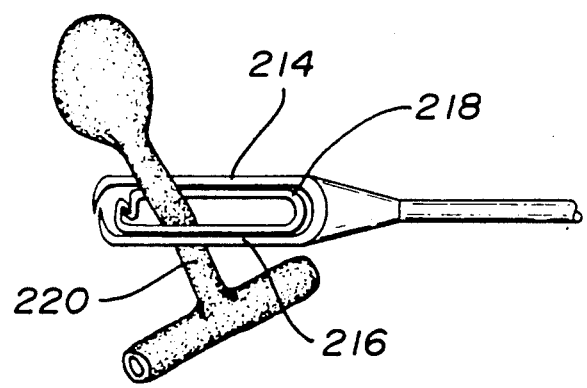
Figure 21D:
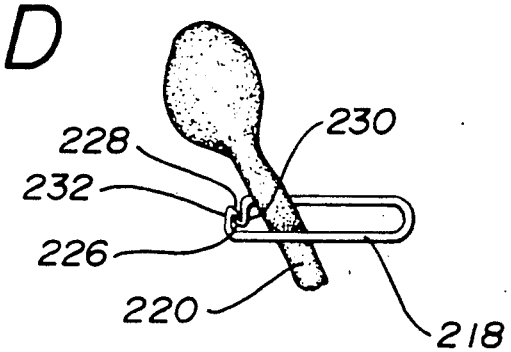

Upon ejection of staple 198 from channel 196, the surgeon opens jaws 200 and 202 of forceps member 194, for example, by pushing an elongate flexible rod member 142 (FIGS. 16–19). The opening of jaws 200 and 202 permits staple 198 to open from a closed prefiring configuration to an opened configuration (FIG. 20B). Forceps member 194 is then pushed further in the distal direction to move the opened staple 298 and jaws 200 and 202 into internal body tissues 192, as shown in FIG. 20C. Upon contact between jaws 200 and 202 and the internal body tissues 192, the surgeon operates forceps member 194 to close the jaws, thereby grasping the internal body tissues between gripping teeth 210 and 212 of jaws 200 and 202 and closing staple 198 in the body tissues about wound 208.

The closing of staple 198 automatically locks the staple in the closed configuration owing to locking hook elements 204 and 206. Upon the locking of staple 198, the surgeon opens jaws 200 and 202 to release said internal body tissues. The forceps member 194 is then retracted into the biopsy channel 196 of endoscope member 190, which is then withdrawn from the patient.

The opening and closing of jaws 200 and 202 may be accomplished as described hereinabove with reference to FIGS. 1619 or by any other means suitable in the art.

FIGS. 21A through 21D illustrate the use of an endoscopic stapling device with forceps jaws 214 and 216 and an open-biased staple 218 to close a duct 220 in a patient's body. Staple 218 is provided with locking elements 222 and 224 having distally and proximally facing hooks 226 and 228 which engage one another to lock the staple upon closure thereof about duct 220. Locking elements 222 and 224 having proximally and distally facing smooth surfaces 230 and 232 which contact one another in the closed prefiring configuration of staple 218.

As illustrated in FIG. 22, another endoscopic stapling device comprises a pneumatic or hydraulic cylinder 234 operatively connected to forceps jaws 236 via a schematically indicated plunger and linkage mechanism 238 which may be similar to actuator plate 144, slots 146 and 148, pins 150 and 152, and fingers or levers 154 and 156. Cylinder 234 is fed with pressurized air or liquid from a reservoir or source 240 via a manually operable valve 242.

A staple 174, 198 pr 218 is loadable between respective forceps jaws by withdrawing the entire flexible forceps from the endoscopic member with which the forceps is being used.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A surgical instrument comprising:
   an endoscope including an elongate flexible outer tubular member and a biopsy channel extending longitudinally through said tubular member;
   an elongate flexible forceps member slidably disposed in said biopsy channel, said forceps member being provided at a distal end with a pair of forceps jaws each formed on an inwardly facing surface with a longitudinally extending groove; actuating means for manipulating said jaws between and open and closed position; and
   a staple having a spring bias tending to force said staple into an opened configuration, said staple being disposed in a closed prefiring configuration between said jaws when said jaws are closed, said staple having legs each disposed in said closed prefiring configuration in a respective one of the grooves, said staple having interlocking means for locking said staple in a closed postfiring configuration in opposition to said spring bias.

2. The surgical instrument set forth in claim 1 wherein said jaws are provided at distal ends with inwardly turned portions in turn formed with means for gripping internal body tissues.

3. The surgical instrument set forth in claim 1 wherein said staple has a pair of legs joined by a bight portion, said means includes interlocking a pair of interlocking hook elements on said legs.

4. The surgical instrument set forth in claim 3 wherein said interlocking hook elements each includes a hook side and a smooth side, the smooth sides of said interlocking hook elements engaging one another and the hook sides of said interlocking hook elements facing away from one another in said closed prefiring configuration.

5. The surgical instrument set forth in claim 3 wherein said interlocking hook elements are disposed at the distal ends of said legs.

6. The surgical instrument set forth in claim 3 wherein said interlocking hook elements are disposed proximally of the distal ends of said legs.

7. The surgical instrument set forth in claim 3 wherein said interlocking hook elements are disposed proximately to said bight portion.

8. A surgical instrument comprising:
   an elongate flexible forceps member having a diameter sufficiently small so that said forceps member is slidably insertable into a biopsy channel extending longitudinally through a flexible tubular endoscope member, said forceps member being provided at a distal end with a pair of forceps jaws each formed on an inwardly facing surface with a longitudinally extending groove; actuating means for manipulating said jaws between and open and closed position; and
   a staple having a spring bias tending to force said staple into an opened configuration, said staple being disposed in a closed prefiring configuration between said jaws when said jaws are closed, said staple having legs each disposed in said closed prefiring configuration in a respective one of the grooves, said staple having interlocking means for locking said staple in a closed postfiring configuration in opposition to said spring bias.

9. The surgical instrument set forth in claim 8 wherein said jaws are provided at a distal end with an inwardly turned portion in turn formed with means for gripping internal body tissues.

10. The surgical instrument set forth in claim 8 wherein said staple has a pair of legs joined by a bight portion, said interlocking means taking the form of a pair of interlocking hook elements on said legs.

11. The surgical instrument set forth in claim 10 wherein said interlocking hook elements each includes a hook side and a smooth side, the smooth sides of said interlocking hook elements engaging one another and the hook sides of said interlocking hook elements facing away from one another in said closed prefiring configuration.

12. The surgical instrument set forth in claim 10 wherein said interlocking hook elements are disposed at the distal ends of said legs.

13. The surgical instrument set forth in claim 10 wherein said interlocking hook elements are disposed proximally of the distal ends of said legs.

14. The surgical instrument set forth in claim 10 wherein said interlocking hook elements ar disposed proximately to said bight portion.

15. A surgical instrument comprising:
an elongate flexible forceps member having a diameter sufficiently small so that said forceps member is slidably insertable into a biopsy channel extending longitudinally through a flexible tubular endoscope member, said forceps member being provided at a distal end with a pair of forceps jaws each formed at a distal end with an inwardly turned portion in turn formed with means for gripping internal body tissues; actuating means for manipulating said jaws between an open and closed position; and
a staple disposed in a closed prefiring configuration between said jaws when said jaws are closed, said staple having a spring bias tending to force said staple into an opened configuration;
mounting means on said jaws for holding said staple between said jaws; and
means for locking said staple in a closed prefiring configuration in opposition to said spring bias said means for locking including interlocking elements.

16. The surgical instrument set forth in claim 15 wherein said mounting means includes grooves formed on inwardly faces sides of said jaws, said staple having legs seated in said grooves.

17. The surgical instrument set forth in claim 15 wherein said interlocking elements take the form of a pair of interlocking hook elements on said legs.

18. The surgical instrument set forth in claim 17 wherein said interlocking hook elements each includes a hook side and a smooth side, the smooth sides of said interlocking hook elements engaging one another and the hook sides of said interlocking hook elements facing away from one another in said closed prefiring configuration.

19. The surgical instrument set forth in claim 17 wherein said interlocking hook elements are disposed at the distal ends of said legs.

20. The surgical instrument set forth in claim 17 wherein said interlocking hook elements are disposed proximally of the distal ends of said legs.

21. The surgical instrument set forth in claim 17 wherein said interlocking hook elements are disposed proximately to said bight portion.

* * * * *

UNITED STATES PATENT AND TRADEMARK OFFICE
CERTIFICATE OF CORRECTION

PATENT NO. : 5,049,153

DATED : September 17, 1991

INVENTOR(S) : Naomi L. Nakao and Peter J. Wilk

It is certified that error appears in the above-identified patent and that said Letters Patent is hereby corrected as shown below:

In the Abstract, line 13, after "The" insert --staple is--.

Column 2, line 26, insert --.-- (period) after "jaws"; line 34, change "faces" to --facing--.

Column 3, line 32, change "though" to --through--; line 66, change "Figs. 8A-8F" to --Figs. 7A-7F--.

Column 7, line 28, change "2b" to --62b--.

Column 11, line 39, change "1619" to --16-19--; line 60, change "pr" to --or--.

Column 12,
Claim 1, line 10, change "and" (first occurrence) to --an--.

Claim 8, line 10, change "and" (first occurrence) to --an--.

UNITED STATES PATENT AND TRADEMARK OFFICE
CERTIFICATE OF CORRECTION

PATENT NO. : 5,049,153
DATED : September 17, 1991
INVENTOR(S) : Naomi L. Nakao and Peter J. Wilk It is certified that error appears in the above-indentified patent and that said Letters Patent is hereby corrected as shown below:

Column 13, claim 14, line 2, change "ar" to --are--.
Column 14, claim 16, line 3, change "faces" to --facing--.

Signed and Sealed this

Eighth Day of November, 1994

Attest:

BRUCE LEHMAN

Attesting Officer

Commissioner of Patents and Trademarks